US009353170B2

(12) United States Patent
Hersel et al.

(10) Patent No.: US 9,353,170 B2
(45) Date of Patent: May 31, 2016

(54) LONG-ACTING TRANSIENT POLYMER CONJUGATES OF EXENDIN

(75) Inventors: Ulrich Hersel, Heidelberg (DE); Harald Rau, Heidelberg (DE); Dirk Vetter, Heidelberg (DE); Thomas Wegge, Heidelberg (DE)

(73) Assignee: SANOFI-AVENTIS DEUTSCHLAND GMBH, Deutschland (DE)

( * ) Notice: Subject to any disclaimer, the term of this patent is extended or adjusted under 35 U.S.C. 154(b) by 1375 days.

(21) Appl. No.: 12/663,628

(22) PCT Filed: Jun. 5, 2008

(86) PCT No.: PCT/EP2008/056981
§ 371 (c)(1),
(2), (4) Date: Sep. 15, 2010

(87) PCT Pub. No.: WO2008/148839
PCT Pub. Date: Dec. 11, 2008

(65) Prior Publication Data
US 2011/0009315 A1    Jan. 13, 2011

(30) Foreign Application Priority Data
Jun. 8, 2007 (EP) .................................... 07109895

(51) Int. Cl.
C07K 14/575 (2006.01)
A61K 47/48 (2006.01)
A61K 38/00 (2006.01)

(52) U.S. Cl.
CPC ........ *C07K 14/57563* (2013.01); *A61K 47/4823* (2013.01); *A61K 47/48215* (2013.01); *A61K 47/48238* (2013.01); *A61K 47/48284* (2013.01); *A61K 47/48338* (2013.01); *A61K 38/00* (2013.01)

(58) Field of Classification Search
None
See application file for complete search history.

(56) References Cited

U.S. PATENT DOCUMENTS

| 5,424,286 | A | 6/1995 | Eng |
| 6,506,724 | B1 | 1/2003 | Hiles et al. |
| 7,157,555 | B1 | 1/2007 | Beeley et al. |
| 8,377,917 | B2* | 2/2013 | Hersel et al. ................. 514/183 |
| 2008/0241102 | A1* | 10/2008 | Hersel et al. ................. 424/85.4 |
| 2010/0291021 | A1* | 11/2010 | Vetter et al. ................. 424/78.36 |
| 2011/0009315 | A1* | 1/2011 | Hersel et al. ................. 514/7.2 |

FOREIGN PATENT DOCUMENTS

| EP | 1 845 105 A1 | 10/2007 |
| WO | WO 99/25727 | 5/1999 |
| WO | WO 99/25728 | 5/1999 |
| WO | WO 99/40788 | 8/1999 |
| WO | WO-00/66629 A1 | 11/2000 |
| WO | WO 2005/034909 | 4/2005 |
| WO | WO 2005/099768 | 10/2005 |
| WO | WO2005/099769 | 10/2005 |
| WO | WO 2005099768 | * 10/2005 | ............ A61K 47/48 |
| WO | WO 2006/003014 | 1/2006 |
| WO | WO-2006/087354 A2 | 8/2006 |
| WO | WO-2006/087354 A3 | 8/2006 |
| WO | WO-2006/124529 A1 | 11/2006 |
| WO | WO2006/136586 | 12/2006 |
| WO | WO 2006/136586 | 12/2006 |
| WO | WO 2006136586 | * 12/2006 | ............ A61K 47/48 |
| WO | WO 2007/053946 | 5/2007 |
| WO | WO-2007/075534 A2 | 7/2007 |
| WO | WO-2007/075534 A3 | 7/2007 |
| WO | WO2008/116913 | 10/2008 |
| WO | WO 2008/148839 A2 | 12/2008 |

OTHER PUBLICATIONS

Tsubery, H et al., "Prolonging the action of protein and peptide drugs by a novel approach of reversible polyethylene glycol modification", J. of Biolo. Chem., Sep. 10, 2004, pp. 38118-38124, vol. 279, No. 37.*
Shechter et al. (2003) [2-Sulfo-9-fluorenylmethoxycarbonyl]3-exendin-4-a long-acting glucose-lowering prodrug; Biochem. Biophys. Res. Commun. 305(2):386-391.*
Tsubery, H et al., "Prolonging the action of protein and peptide drugs by a novel approach of reversible polyethylene glycol modification", J. of Biolo. Chem., Sep. 10, 2004, pp. 38118-38124, vol. 279, No. 37, US.
Ratner, R et al., "Long-term effects of exenatide therapy over 82 weeks on glycaemic control and weight in over-weight metformin-treated patients with type 2 diabetes mellitus", Diabetes, Obesity & Metabolism, Jul. 2006, pp. 419-428, vol. 8, No. 4.
Linnebjerg, H et al., "Exenatide: Effect of injection time on postprandial glucose in patients with Type 2 diabetes", Diabetic Medicine, 2006, pp. 240-245, vol. 23, No. 3, United Kingdom.
Göke, R et al., "Exendin-4 Is a High Potency Agonist and Truncated Exendin-(9-39)-amide an Antagonist at the Glucagon-like Peptide 1-(7-36)-amide Receptor of Insulin-secreting β-Cells", J. of Biolo. Chem., Sep. 15, 1993, pp. 19650-19655, vol. 268, No. 26, US.
Gutniak, M et al., "Antidiabetogenic effect of glucagon-like peptide-1 (7-36)amide in normal subjects and patients with diabetes mellitus", NE J. of Med., May 14, 1992, pp. 1316-1322, vol. 326, No. 20.
Young, A et al., "Glucose-Lowering and Insulin-Sensitizing Actions of Exendin-4: Studies in Obese Diabetic (ob/ob, db/db) Mice, Diabetic Fatty Zucker Rats, and Diabetic Rhesus Monkeys (*Macaca mulatta*)", Diabetes, May 1999, pp. 1026-1034, vol. 48.
Edwards, C.M.B. et al., "Exendin-4 reduces fasting and postprandial glucose and decreases energy intake in healthy volunteers", Am. J. Physiol. Endocrinol. Metab. 2001, pp. 155-161, vol. 281, US.
Fehse, F et al., "Exenatide Augments First- and Second-Phase Insulin Secretion in Response to Intravenous Glucose in Subjects with Type 2 Diabetes", J Clin. Endocrinol. Metab., 2005, pp. 5991-5997, vol. 90, No. 11, US.

(Continued)

*Primary Examiner* — Maury Audet
(74) *Attorney, Agent, or Firm* — Morrison & Foerster LLP

(57) ABSTRACT

Long-acting polymer exendin-4 or exendin agonist derivatives of the formula Pol-L-E are provided wherein Pol is a polymer, L is a releasing linker undergoing slow autohydrolysis and E is an exendin or exendin agonist. These exendin or exendin agonists are slowly released from Pol-L upon administration to a living organism. The derivatives are useful e.g. for the treatment of diabetes mellitus.

13 Claims, 6 Drawing Sheets

(56) References Cited

OTHER PUBLICATIONS

Dupré, J et al., "Exendin-4 Normalized Postcibal Glycemic Excursions in Type 1 Diabetes", J Clin. Endocrinol. Metab., 2004, pp. 3469-3473, vol. 89, No. 7, US.

Pérez-Tilve, D et al., "Exendin-4 Potently Decreases Ghrelin Levels in Fasting Rats", Diabetes, Jan. 2007, pp. 143-151, vol. 56, US.

Nauck, M et al., "Glucagon-like peptide 1 and its derivatives in the treatment of diabetes", Regulatory Peptides, 2005, pp. 135-148, vol. 128.

Kim, D et al., "Effects of Once-Weekly Dosing of a Long-Acting Release Formulation of Exenatide on Glucose Control and Body Weight in Subjects With Type 2 Diabetes", Diabetes Care, Jun. 2007, pp. 1487-1493, vol. 30, No. 6.

Shechter, Y et al., "[2-Sulfo-9-fluorenylmethoxycarbonyl]$_3$-exendin-4-a long-acting glucose-lowering prodrug", Biochem, Biophys. Res. Commun., 2003, pp. 386-391, vol. 305.

Lee, S, et al., "Synthesis, Characterization, and Pharmacokinetic Studies of PEGylated Glucagon-like Peptide-1", Bioconjug. Chem., 2005, pp. 377-382, vol. 16, No. 2.

De Fronzo, R et al., "Effects of Exenatide (Exendin-4) on Glycemic Control and Weight Over 30 Weeks in Metformin-Treated Patients With Type 2 Diabetes", Diabetes Care, May 2005, pp. 1092-1100, vol. 28, No. 5.

Peppas, N et al., "Hydrogels in pharmaceutical formulations", Eur. J. Pharm. Biopharm., 2000, pp. 27-46, vol. 50.

Hennink, W et al., "Novel crosslinking methods to design hydrogels", Adv. Drug Del. Rev., 2002, pp. 13-36, vol. 54.

Boas, U et al., "Dendrimers in drug research", Chem. Soc. Rev., 2004, pp. 43-63, vol. 33.

Esfand, R et al., "Poly(amidoamine) (PAMAM) dendrimers: from biomimicry to drug delivery and biomedical applications", Drug Discov Today, Apr. 2001, pp. 427-436, vol. 6, No. 8, US.

Grayson, S et al., "Convergent Dendrons and Dendrimers: from Synthesis to Applications", Chem. Rev., 2001, pp. 3819-3867, vol. 101, Berkeley, CA, US.

Tsubery, H et al., "Prolonging the action of protein and peptide drugs by a novel approach of reversible polyethylene glycol modification", Journal of Biological Chemistry, Sep. 10, 2004, pp. 38118-38124, vol. 279, No. 37, American Society of Biolochemical Biologists, Birmingham, US.

Linnebjerg, H et al., "Exenatide: Effect of injection time on postprandial glucose in patients with Type 2 diabetes", Diabetic Medicin, 2003, pp. 240-245, vol. 23, No. 3, United Kingdom.

Greig, N. et al., "New therapeutic strategies and drug candidates for neurodegenerative diseases: p53 and TNF-alpha inhibitors, and GLP-1 receptor agonists", Annals of the New York Academy of Sciences Dec. 2004, pp. 290-315, vol. 1035.

"Material Safety Data Sheet-40 kDa Methoxy Poly(Ethylene Glycol) Maleimido-Propionamide", ChiroTech Technology Ltd.—Product No. 008-016, No. 1, 2 pages (Feb. 14, 2005).

Wathier, M., et ai,, "Dendritic Macromers as in Situ Polymerizing Biomaterials for Securing Cataract Incisions" J. Am. Chem. Soc. 126:12744-12745 (2004).

Izutsu, K., "Stabilization of Therapeutic Proteins by Chemical and Physical Methods" Methods in Molecular Biology 308:287-292 (2005).

Crosslinking Technical Handbook, from Thermo Scientific, published on Apr. 2009, pp. 1-48.

Office Action issued on Jun. 23, 2014 in U.S. Appl. No. 13/387,940.

Office Action issued in U.S. Appl. No. 13/387,959 dated Nov. 28, 2014.

International Search Report mailed on Jun. 26, 2009, for PCT Patent Application No. PCT/EP2008/056981, filed on Jun. 5, 2008, ten pages.

Written Opinion of the International Searching Authority mailed on Jun. 26, 2009, for PCT Patent Application No. PCT/EP2008/056981, filed on Jun. 5, 2008, twelve pages.

\* cited by examiner

LONG-ACTING TRANSIENT POLYMER CONJUGATES OF EXENDIN

This application is a 371 of international patent application Serial No. PCT/EP2008/056981 filed Jun. 5, 2008, which claims priority to EP patent application Serial No. 07109895.8 filed Jun. 8, 2007.

The present invention relates to a class of novel long-acting transient polymer conjugates of exendins and exendin agonists. These conjugates of exendins and exendin agonists following administration are capable of undergoing spontaneous chemical transformation in the living organism from an essentially inactive into a bioactive form. The invention also relates to polymer conjugates of exendins and exendin agonists bearing functional groups sensitive to neutral aqueous conditions, and to pharmaceutical compositions comprising them. The conjugates are particularly useful for prevention of hyperglycemia, treatment of diabetes mellitus, treatment of disorders which would be benefited with agents useful in delaying and/or slowing gastric emptying and treatment of obesity.

Exendin-4 is a 39-amino acid peptide, isolated from the salivary secretions of the venomous Gila monster (*Heloderma suspectum*). It has some sequence similarity to several members of the glucagon-like peptide family, with the highest homology of 53%, being to glucagon-like peptide-1 [7-36]-amide (GLP-1). Exendin-4 acts as a GLP-1 agonist on the GLP-1 receptor and bears GLP-1-like insulin secretagogue action in isolated rat islets. Exendin-4 is a high potency agonist and truncated exendin-(9-39)-amide an antagonist at the glucagon-like peptide 1-(7-36)-amide receptor of insulin-secreting beta-cells. (see e.g. J. Biol. Chem. 268(26):19650-19655). Exendin-4 ("exenatide") was approved recently in the US and EU for improving glycemic control in patients with type 2 diabetes taking metformin and/or a sulfonylurea but have not achieved adequate glycemic control.

GLP-1 is one of the intestinal peptide hormones that are released into the circulatory system after food intake. It augments the postprandial release of insulin, when nutritions (especially carbohydrates) are absorbed and their level postprandially elevated.

GLP-1 associates with GLP-1 receptor sites located on pancreatic β-cells and elevates endogenous cAMP levels in a dose dependent manner. In isolated rat islets in the presence of above normoglycemic glucose levels, GLP-1 stimulates the release of insulin.

A therapeutic potential for GLP-1 in type 2 diabetes patients was suggested before, owing to the profound efficacy of this insulinotropic peptide to stimulate secretion of insulin when glucose levels are elevated and to cease doing so upon return to normoglycemia. The antidiabetogenic effect of glucagon-like peptide-1 (7-36) amide in normal subjects and patients with diabetes mellitus is described e.g. in N. Engl. J. Med. 326(20):1316-1322.

In vitro studies and animal experiments suggest that GLP-1 improves insulin sensitivity and has an anabolic effect on pancreatic β-cells. In humans, GLP-1 was also reported to suppress glucagon secretion, decelerate gastric emptying, and induce satiety, leading to weight loss if administered for weeks and months.

Exendin-4 is reported to associate with GLP-1 receptors located on pancreatic beta-cells with 2.5 times higher affinity than GLP-1. In isolated rat islets and beta-cells in presence of glucose, exendin enhances secretion of insulin in a dose-dependent fashion. Exendin-4 is a high potency agonist and truncated exendin-(9-39)-amide an antagonist at the glucagon-like peptide 1-(7-36)-amide receptor of insulin-secreting beta-cells (see J. Biol. Chem. 268(26):19650-19655). Studies in type 2 diabetic rodents revealed that exendin-4 is 5530-fold more potent than GLP-1 in lowering blood glucose levels. Also, the duration of glucose-lowering action after a single administration of exendin-4 is significantly longer compared to GLP-1 (see e.g. Diabetes 48(5):1026-1034). Plasma half-life of exendin-4 in humans was described to be only 26 minutes. Exendin-4 reduces fasting and postprandial glucose and decreases energy intake in healthy volunteers (see e.g. Am. J. Physiol. Endocrinol. Metab. 281(1):E155-61).

In clinical studies postprandial glucose lowering action of exendin-4 in humans was shown if administered 60-0 minutes before a meal (see Linnebjerg H., et al., (2006), Diabet. Med. 23(3):240-245). First phase and second phase insulin response was increased and plasma glucagon was decreased after intravenous glucose bolus (see Fehse F. et al., (2005), J. Clin. Endocrinol. Metab. 90(11):5991-5997). Exendin-4 displayed a delay in gastric emptying and reduced food intake at a buffet lunch by 19% in healthy subjects (see Edwards C. M. et al., (2001), Am. J. Physiol. Endocrinol. Metab. 281(1): E155-61).

Long term benefits of 82 weeks exenatide-4 therapy in diabetic patients receiving exendin-4 and metformin include improved glycemic control as assessed by durable reductions in haemoglobin A1c (HbA1c) value, weight reduction and additional significant improvements of cardiovascular risk factors (see Ratner R. E., et al., (2006), *Diabetes Obes. Metab.* 8(4):419-428). The usefulness of exendin-4 in type 1 diabetes therapy was shown (see e.g. Dupré J., et al., (2004), *J. Clin. Endocrinol. Metab.* 89(7):3469-3473).

Supression of hunger hormone ghrelin in rats by exendin-4 was described which could not be mimicked by GLP-1. This adds further evidence to observations, that some effects of exendin-4 can not be explained by activation of GLP-1 receptor (see Pérez-Tilve D. et al., 2007, *Diabetes.* 56(1):143-151).

Current therapy with exenatide requires frequent injections (bidaily) resulting in high plasma levels after injection, which is correlated to nausea (see Nauck M. A., Meier J. J. (2005), *Regul Pept.* 128(2):135-148), and to low trough concentrations, leading to incomplete glycemic control (see Kim D., et al. (2007), *Diabetes Care.* 30(6):1487-1493). To overcome these problems a longer-acting formulation for exendin-4 is highly desirable. Ideally, the peptide is formulated in a fashion that provides for a sustained plasma level in human for at least one week after application to a human body resulting in a once-weekly or longer injection frequency. Several long-acting exendins have been proposed.

In one approach, three moieties of 2-sulfo-9-fluorenylmethoxycarbonyl (FMS) have been linked to the three amino groups of exendin-4 ($FMS_3$-exendin-4), generating a prodrug with 0.1% glucose-lowering potency of the native peptide (see Shechter et al. (2003) [2-Sulfo-9-fluorenylmethoxycarbonyl]3-exendin-4-a long-acting glucose-lowering prodrug; *Biochem. Biophys. Res. Commun.* 305(2):386-391). FMS cleavage out of $FMS_3$-exendin-4 leads to regeneration of the amino groups of exendins-4 with a half-life of 18 h after incubation in a human plasma model, with cleavage being complete at 40 h. In diabetic db/db mice $FMS_3$-exendin-4 (10 μg/mouse subcutaneously) showed a sustained 50% reduction in blood glucose, returning to baseline value after 45 h. $FMS_3$-exendin-4, subject to rapid renal clearance due to its small size, may exert its prolonged effect due to precipitation or binding to plasma protein, e.g. albumin (see Shechter et al. (2003), *Biochem. Biophys. Res. Commun.* 305(2):386-391).

The disadvantage of this approach is the presence of several different FMS-exendin conjugates in vivo as the FMS linkers are sequentially cleaved from the FMS$_3$-exendin-4 parent molecule resulting in heterogeneous pharmacology.

A further approach is the permanent covalent attachment of a polymeric carrier molecule to the exendin peptide. Conjugation to polymeric carrier like poly(ethylene glycol) (PEG) or human serum albumin greatly reduces renal elimination and shields from proteases and the immune system. For example, WO 2007/053946A1 discloses a permanent human serum albumin conjugate of Exendin-4.

However, conjugation of a polymer to a peptide results in significant loss of receptor affinity and bioactivity. For example, N-terminal PEGylation of GLP-1 with only PEG2kDa nearly completely abolished its activity on stimulating insulin release from rat pancreas islets (see Lee S. H., et al. (2005) *Bioconjug. Chem.* 16(2):377-382). N-terminal PEGylation of Exendin-4 results in only approximately 1% residual activity compared to the native peptide (see Tsubery, et al. (2004) *J. Biol. Chem.* 279(37):38118-38124). Furthermore, the distribution of the conjugate in the body differs significantly from the native peptide, potentially resulting in different pharmacological actions.

In another approach exendin-4 was formulated in biodegradable poly-lactide-glycolide based microspheres. Clinical data after 15 weeks of once weekly injection revealed improved glycemic control and reduced side effects compared to bidaily injections (Kim D. et al. (2007); *Diabetes Care.* 30(6):1487-1493). The advantage of this approach is the release of the native exendin molecule with its full and unchanged pharmacology.

However, disadvantages of this approach are general difficulties with microsphere formulations like initial burst problem, large needle diameters for injection, modification of drug during microsphere degradation and difficult manufacturability, combined with very high interpatient variability of exendin-4 plasma levels after 15 weeks and prevalence of antibody formation in 67% patients after 15 weeks versus in 43% patients after 30 weeks of exendin bidaily, which still need to be resolved (see DeFronzo R. A et al. (2005), *Diabetes Care.* 28(5):1092-1100 and *Diabetes Care.* 30(6):1487-1493).

Transient polymer conjugation combines the advantages of prolonged circulation times due to polymer attachment and the recovery of the original pharmacology of the native peptide after release from the polymer conjugate.

Using polymer-linker peptide conjugates, native unchanged peptide is slowly released after injection into a body, governed only by release kinetics of traceless linker and pharmacokinetics of the polymer carrier. Ideally, release kinetics would be independent from the presence of enzymes like proteases or esterases in body fluids to guarantee a consistent and homogenous release pattern.

Shechter et al. presented a system of transiently PEGylated Exendin-4 based on a traceless FMS-linker. Upon subcutaneous injection, PEG40 kDa-FMS-exendin-4 maintained a glucose lowering effect of 30% for 24 h in normoglycaemic mice (see Shechter Y. et al. (2004), *J. Biol. Chem.* 279(37): 38118-38124). However, Exendin-4 was cleaved from PEG40 kDa-FMS-exendin-4 with a half-life of 12 h in a human plasma model. This half-life is too short to achieve a sustained plasma level over one week and a once-weekly injection regime. Linker molecules with longer half-lives have to be used to achieve this goal.

Linker molecules suitable for transient polymer conjugation have been described by Complex Biosystems for example in WO 2006/136586 (aliphatic prodrug linkers) and WO 2005/099768 (cyclic prodrug linkers). These linkers provide for slower cleavage kinetics as compared to the above mentioned FMS-linker and are useful for once-weekly injection regime.

Various Exendin agonists furthermore have been described in U.S. Pat. No. 5,424,286, U.S. Pat. No. 6,506,724, U.S. Pat. No. 7,157,555, WO 1999/25727, WO 1999/25728 and WO 1999/40788.

The present invention is directed to a polymeric compound of the general formula (I)

$$\text{Pol-L-E} \tag{I}$$

wherein Pol is a polymer,

L is a releasing linker undergoing autohydrolysis and

E is exendin or an exendin agonist.

In this polymer, which can act as a prodrug, the bond between L and E is hydrolysed under in vivo conditions at a pH-value between 7.0 and 7.5 and a temperature of 36° to 38° C. and in human plasma with a half-life of 24 hours or more.

In a preferred embodiment, in the polymeric compound (I) Pol is a polyalkyloxy-based polymer, L is a releasing linker consisting of neighbouring groups catalyzing hydrolysis of a transient linkage, and E is exendin or an exendin agonist. In this polymeric compound the bond between L and E is hydrolysed under in vivo conditions at a pH-value between 7.0 and 7.5 and a temperature of 36° C. to 38° C. and in human plasma with a half-life between 24 hours and 100 days. Preferably, the half-life is between 2 days and 80 days, more preferably between 4 days and 60 days, even more preferably between 7 days and 40 days and most preferably the half-life is between 28 days and 31 days.

Preferred embodiments of these polymers of formula (I) are the structures of the following five formulae Ia, Ib, Ic, Id, and Ie. These polymeric compounds are hydrolysed under in vivo conditions at a pH-value between 7.0 and 7.5 and a temperature of 36° C. to 38° C. and in human plasma with a half-life of 24 hours or more, and they all can thereby release the active principle E.

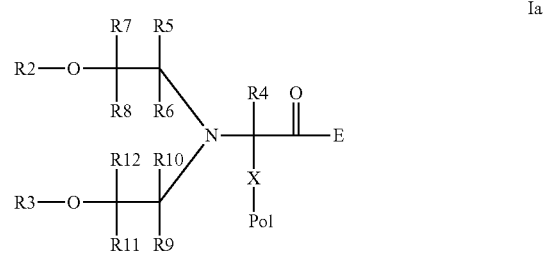

Ia

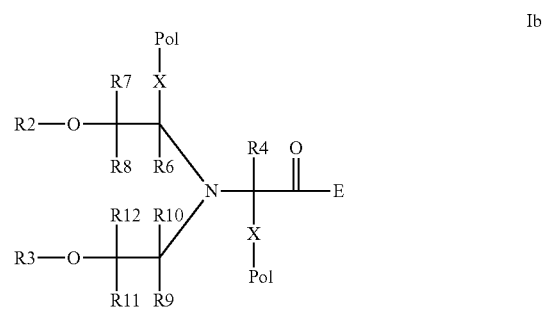

Ib

-continued

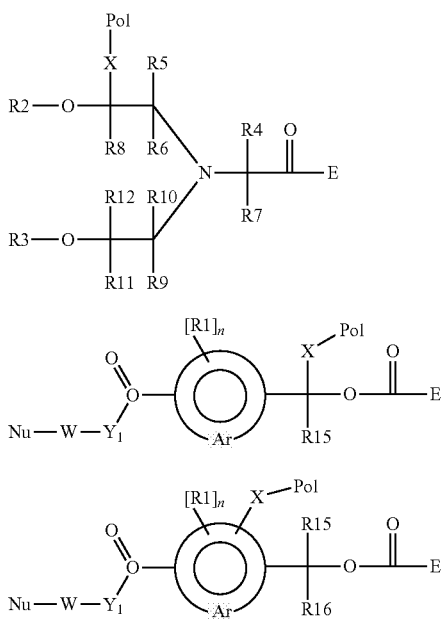

The invention in particular relates to a polymeric compound having the following structure (Ia):

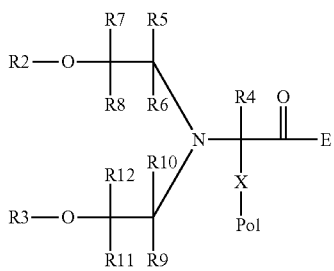

wherein the substituents have the following meanings:
E is exendin or an exendin agonist,
X is a spacer moiety $R13\text{-}Y_2$,
$Y_2$ is O, S, NR14, succinimide, maleimide, unsaturated carbon-carbon bonds or any heteratom containing a free electron pair or is absent,
R13 is selected from substituted or non-substituted linear, branched or cyclical alkyl or heteroalkyl, aryls, substituted aryls, substituted or non-substituted heteroaryls,
R14 is selected from hydrogen, substituted or non-substituted linear, branched or cyclical alkyl or heteroalkyl, aryls, substituted aryls, substituted or non-substituted heteroaryls;
R2 and R3 are selected independently from hydrogen or acyl groups,
R4 to R12 are selected independently from hydrogen, X-Pol, substituted or non-substituted linear, branched or cyclical alkyl or heteroalkyl, aryls, substituted aryls, substituted or non-substituted heteroaryls, cyano, nitro, halogen, carboxy, carboxamide, and
Pol is a polymer.

Preferred polymeric compound have structure (Ia), wherein E is exendin or an exendin agonist; X is a spacer moiety $R13\text{-}Y_2$, $Y_2$ is O, S, NR14, succinimide, unsaturated carbon-carbon bonds or is absent,
R13 is selected from non-substituted linear, branched or cyclical C1 to C12 alkyl or heteroalkyl, aryls, aryls, or non-substituted heteroaryls,
R14 is selected from hydrogen, non-substituted linear, branched or cyclical C1 to C8 alkyl or heteroalkyl, aryls, or non-substituted heteroaryls;
R2 and R3 are selected independently from hydrogen or C1 to C6 acyl groups.
R4 to R12 are selected independently from hydrogen, X-Pol, non-substituted linear, branched or cyclical C1 to C8 alkyl or heteroalkyl, aryls, non-substituted heteroaryls, cyano, nitro, halogen, carboxy, carboxamide; and
Pol is poly(propylene glycol), poly(ethylene glycol), dextran, chitosan, hyaluronic acid, alginate, xylan, mannan, carrageenan, agarose, cellulose, starch, hydroxyethyl starch (HES), poly(vinyl alcohols), poly(oxazolines), poly(anhydrides), poly(ortho esters), poly(carbonates), poly(urethanes), poly(acrylic acids), poly(acrylamides), HMPA), poly(acrylates), poly(methacrylates), poly(organophosphazenes), poly(siloxanes), poly(vinylpyrrolidone), poly(cyanoacrylates), poly(esters), poly(iminocarbonates), poly(amino acids), collagen, gelatin, or albumin.

The invention in particular relates to a polymeric compound having the following structure (Ib):

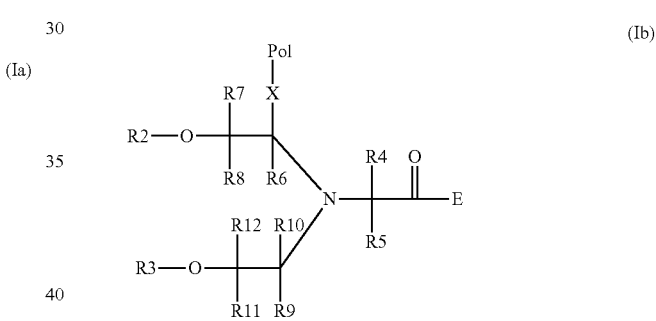

wherein
E is exendin or an exendin agonist,
X is a spacer moiety such as $R13\text{-}Y_2$,
$Y_2$ is O, S, NR14, succinimide, maleimide, unsaturated carbon-carbon bonds or any heteratom containing a free electron pair or is absent,
R13 is selected from substituted or non-substituted linear, branched or cyclical alkyl or heteroalkyl, aryls, substituted aryls, substituted or non-substituted heteroaryls,
R14 is selected from hydrogen, substituted or non-substituted linear, branched or cyclical alkyl or heteroalkyl, aryls, substituted aryls, substituted or non-substituted heteroaryls;
R2 and R3 are selected independently from hydrogen or acyl groups,
R4 to R12 are selected independently from hydrogen, X-Pol, substituted or non-substituted linear, branched or cyclical alkyl or heteroalkyl, aryls, substituted aryls, substituted or non-substituted heteroaryls, cyano, nitro, halogen, carboxy, carboxamide,
Pol is a polymer.
In these compounds of structure (Ib) the substituents preferably have the following meaning:
E is exendin or an exendin agonist,
X is a spacer moiety $R13\text{-}Y_2$, $Y_2$ is O, S, NR14, succinimide, unsaturated carbon-carbon bonds or is absent, R13 is selected from non-substituted linear, branched or cyclical C1 to C12 alkyl or heteroalkyl, aryls, or non-substituted heteroaryls, R14 is selected from hydrogen, substituted or non-substituted linear, branched or cyclical alkyl or heteroalkyl, aryls, substituted aryls, substituted or non-substituted heteroaryls;

R2 and R3 are selected independently from hydrogen or C1 to C6 acyl groups,

R4 to R12 are selected independently from hydrogen, X-Pol, non-substituted linear, branched or cyclical C1 to C8 alkyl or heteroalkyl, aryls, non-substituted heteroaryls, cyano, nitro, halogen, carboxy, carboxamide, Pol is polypropylene glycol), poly(ethylene glycol), dextran, chitosan, hyaluronic acid, alginate, xylan, mannan, carrageenan, agarose, cellulose, starch, hydroxyethyl starch (HES), poly(vinyl alcohols), poly(oxazolines), poly(anhydrides), poly(ortho esters), poly(carbonates), poly(urethanes), poly(acrylic acids), poly(acrylamides), HMPA), poly(acrylates), poly(methacrylates), poly(organophosphazenes), poly(siloxanes), poly(vinylpyrrolidone), poly(cyanoacrylates), poly(esters), poly(iminocarbonates), poly (amino acids), collagen, gelatin, or albumin.

The invention in particular relates to a polymeric compound having the following structure structure (Ic):

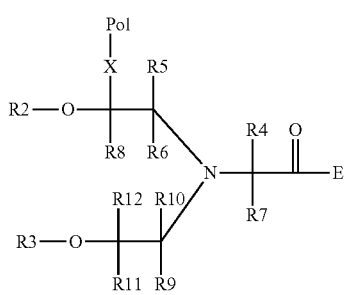

(Ic)

wherein

E is exendin or an exendin agonist,

X is a spacer moiety such as R13-$Y_2$, $Y_2$ is O, S, NR14, succinimide, maleimide, unsaturated carbon-carbon bonds or any heteratom containing a free electron pair or is absent, R13 is selected from substituted or non-substituted linear, branched or cyclical alkyl or heteroalkyl, aryls, substituted aryls, substituted or non-substituted heteroaryls, R14 is selected from hydrogen, non-substituted linear, branched or cyclical C1 to C8 alkyl or heteroalkyl, aryls, or non-substituted heteroaryls;

R2 and R3 are selected independently from hydrogen or acyl groups,

R4 to R12 are selected independently from hydrogen, X-Pol, substituted or non-substituted linear, branched or cyclical alkyl or heteroalkyl, aryls, substituted aryls, substituted or non-substituted heteroaryls, cyano, nitro, halogen, carboxy, carboxamide, and Pol is a polymer.

Compounds of structure (Ic) are preferred, wherein

E is exendin or an exendin agonist,

X is a spacer moiety R13-$Y_2$, $Y_2$ is O, S, NR14, succinimide, unsaturated carbon-carbon or is absent, R13 is selected from non-substituted linear, branched or cyclical C1 to C12 alkyl or heteroalkyl, aryls, or non-substituted heteroaryls, R14 is selected from hydrogen, non-substituted linear, branched or cyclical C1 to C8 alkyl or heteroalkyl, aryls, or non-substituted heteroaryls;

R2 and R3 are selected independently from hydrogen or C1 to C6 acyl groups,

R4 to R12 are selected independently from hydrogen, X-Pol, non-substituted linear, branched or cyclical C1 to C8 alkyl or heteroalkyl, aryls, non-substituted heteroaryls, cyano, nitro, halogen, carboxy, carboxamide;

Pol is polypropylene glycol), poly(ethylene glycol), dextran, chitosan, hyaluronic acid, alginate, xylan, mannan, carrageenan, agarose, cellulose, starch, hydroxyethyl starch (HES), poly(vinyl alcohols), poly(oxazolines), poly(anhydrides), poly(ortho esters), poly(carbonates), poly(urethanes), poly(acrylic acids), poly(acrylamides), HMPA), poly(acrylates), poly(methacrylates), poly(organophosphazenes), poly(siloxanes), poly(vinylpyrrolidone), poly(cyanoacrylates), poly(esters), poly(iminocarbonates), poly(amino acids), collagen, gelatin, or albumin.

The invention in particular relates to a polymeric compound having the following structure structure (Id):

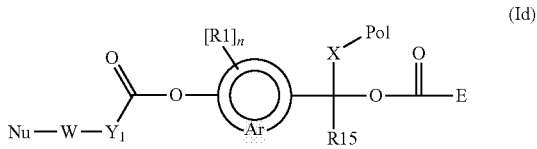

(Id)

wherein

E is exendin or an exendin agonist,

X is a spacer moiety R13-$Y_2$, $Y_1$ is O, NR14, or is absent, $Y_2$ is O, S, NR14, succinimide, unsaturated carbon-carbon bonds or is absent, R15 is selected from hydrogen, substituted or non-substituted linear, branched or cyclical alkyl or heteroalkyl, aryls, substituted aryls, substituted or non-substituted heteroaryls, cyano, nitro, halogen, carboxy, carboxyalkyl, alkylcarbonyl, or carboxamidoalkyl;

R1 is selected independently from hydrogen, substituted or non-substituted linear, branched or cyclical alkyl or heteroalkyl, aryl, substituted aryl, substituted or non-substituted heteroaryl, substituted or non-substituted linear, branched, or cyclical alkoxy, substituted or non-substituted linear, branched, or cyclical heteroalkyloxy, aryloxy, or heteroaryloxy, cyano, halogen;

R13 is selected from substituted or non-substituted linear, branched or cyclical alkyl or heteroalkyl, aryls, substituted aryls, substituted or non-substituted heteroaryls;

R14 is selected from hydrogen, substituted or non-substituted linear, branched or cyclical alkyl or heteroalkyl, aryls, substituted aryls, substituted or non-substituted heteroaryls;

Pol is a polymer;

W is selected from substituted or non-substituted linear, branched or cyclical alkyl, aryls, substituted aryls, substituted or non-substituted linear, branched or cyclical heteroalkyl, substituted or nonsubstituted heteroaryls;
Nu is a nucleophile;
n is zero or a positive integer (e.g. 1 to 10 or 1 to 5) and
Ar is a multi-substituted aromatic hydrocarbon or a multi-substituted aromatic heterocycle.

Polymeric compounds of structure (Id) are preferred wherein:
E is exendin or an exendin agonist,
X is a spacer moiety $R13\text{-}Y_2$,
$Y_1$ is O, NR14, or is absent,
$Y_2$ is O, S, NR14, succinimide, unsaturated carbon-carbon bonds or is absent,
R15 is selected from hydrogen, non-substituted linear, branched or cyclical C1 to C8 alkyl or heteroalkyl, aryls, non-substituted heteroaryls, cyano, nitro, halogen, carboxy, carboxyalkyl, alkylcarbonyl, or carboxamidoalkyl;
R1 is selected independently from hydrogen, non-substituted linear, branched or cyclical C1 to C6 alkyl or heteroalkyl, aryl, non-substituted heteroaryl, cyano, halogen;
R13 is selected from non-substituted linear, branched or cyclical alkyl or heteroalkyl, aryls, or non-substituted heteroaryls;
R14 is selected from hydrogen, non-substituted linear, branched or cyclical C1 to C8 alkyl or heteroalkyl, aryls, or non-substituted heteroaryls;
Pol is polypropylene glycol), poly(ethylene glycol), dextran, chitosan, hyaluronic acid, alginate, xylan, mannan, carrageenan, agarose, cellulose, starch, hydroxyethyl starch (HES), poly(vinyl alcohols), poly(oxazolines), poly(anhydrides), poly(ortho esters), poly(carbonates), poly(urethanes), poly(acrylic acids), poly(acrylamides), HMPA), poly(acrylates), poly(methacrylates), poly(organophosphazenes), poly(siloxanes), poly(vinylpyrrolidone), poly(cyanoacrylates), poly(esters), poly(iminocarbonates), poly(amino acids), collagen, gelatin, or albumin;
W is selected from non-substituted linear, branched or cyclical C1 to C8 alkyl or heteroalkyl, aryls, or nonsubstituted heteroaryls;
Nu is a primary, secondary or tertiary amino group;
n is zero or a positive integer; and
Ar is a multi-substituted C5 or C6 aromatic cycle or heterocycle.

The invention in particular relates to a polymeric compound having the following structure structure (Ie):

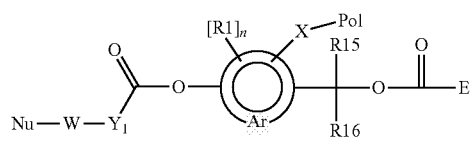

wherein
E is exendin or an exendin agonist,
X is a spacer moiety $R13\text{-}Y_2$
$Y_1$ is O, NR14, or is absent,
$Y_2$ is O, S, NR14, succinimide unsaturated carbon-carbon bonds or any heteratom containing a free electron pair or is absent,
R15 and R16 is selected independently from hydrogen, substituted or non-substituted linear, branched or cyclical alkyl or heteroalkyl, aryls, substituted aryls, substituted or non-substituted heteroaryls, cyano, nitro, halogen, carboxy, carboxyalkyl, alkylcarbonyl, or carboxamidoalkyl;
R1 is selected independently from hydrogen, substituted or non-substituted linear, branched or cyclical alkyl or heteroalkyl, aryl, substituted aryl, substituted or non-substituted heteroaryl, substituted or non-substituted linear, branched, or cyclical alkoxy, substituted or non-substituted linear, branched, or cyclical heteroalkyloxy, aryloxy, or heteroaryloxy, cyano, halogen;
R13 is selected from substituted or non-substituted linear, branched or cyclical alkyl or heteroalkyl, aryls, substituted aryls, substituted or non-substituted heteroaryls;
R14 is selected from hydrogen, substituted or non-substituted linear, branched or cyclical alkyl or heteroalkyl, aryls, substituted aryls, substituted or non-substituted heteroaryls;
Pol is a polymer;
W is selected from substituted or non-substituted linear, branched or cyclical alkyl, aryls, substituted aryls, substituted or non-substituted linear, branched or cyclical heteroalkyl, substituted or nonsubstituted heteroaryls;
Nu is a nucleophile;
n is zero or a positive integer; and
Ar is a multi-substituted aromatic hydrocarbon or a multi-substituted aromatic heterocycle.

Preferred polymeric compounds of structure (Ie) are those, wherein:
E is exendin or an exendin agonist,
X is a spacer moiety $R13\text{-}Y_2$,
$Y_1$ is O, NR14, or is absent,
$Y_2$ is O, S, NR14, succinimide, unsaturated carbon-carbon bonds or is absent,
R15 is selected from hydrogen, non-substituted linear, branched or cyclical C1 to C8 alkyl or heteroalkyl, aryls, non-substituted heteroaryls, cyano, nitro, halogen, carboxy, carboxyalkyl, alkylcarbonyl, or carboxamidoalkyl;
R1 is selected independently from hydrogen, non-substituted linear, branched or cyclical C1 to C6 alkyl or heteroalkyl, aryl, non-substituted heteroaryl, cyano, halogen;
R13 is selected from non-substituted linear, branched or cyclical alkyl or heteroalkyl, aryls, or non-substituted heteroaryls;
R14 is selected from hydrogen, non-substituted linear, branched or cyclical C1 to C8 alkyl or heteroalkyl, aryls, or non-substituted heteroaryls;
Pol is polypropylene glycol), poly(ethylene glycol), dextran, chitosan, hyaluronic acid, alginate, xylan, mannan, carrageenan, agarose, cellulose, starch, hydroxyethyl starch (HES), poly(vinyl alcohols), poly(oxazolines), poly(anhydrides), poly(ortho esters), poly(carbonates), poly(urethanes), poly(acrylic acids), poly(acrylamides), HMPA), poly(acrylates), poly(methacrylates), poly(organophosphazenes), poly(siloxanes), poly(vinylpyrrolidone), poly(cyanoacrylates), poly(esters), poly(iminocarbonates), poly(amino acids), collagen, gelatin, or albumin,
W is selected from non-substituted linear, branched or cyclical C1 to C8 alkyl or heteroalkyl, aryls, or nonsubstituted heteroaryls;
Nu is a primary, secondary or tertiary amino group;
n is zero or a positive integer; and
Ar is a multi-substituted C5 or C6 aromatic cycle or heterocycle.

The term "substituted" in the context of substituted alkyl or heteroalkyl or substituted aryl or heteroaryl means substitution with one or more of any of the functional groups selected independently from hydroxyl, chloride, bromide, fluoride, carboxamide, carboxyl, amino, carbamate, urea, thiourea, thiocarbamate, oxime, cyano, carboxyl, or carbonyl.

As used herein the terms "alkyl" shall mean a monovalent straight chain or branched chain group of 1 or 2 or 3 or 4 or 5 or 6 or 7 or 8 or 9 or 10 or 11 or 12 carbon atoms including, but not limited to, methyl, ethyl, n-propyl, isopropyl, n-butyl, sec-butyl, tert-butyl and the like.

As used herein the terms "cyclical alkyl" shall mean a monovalent cyclic group of 3 or 4 or 5 or 6 or 7 carbon atoms including, but not limited to cyclopropyl, cyclopentyl, cyclohexyl and 4-methyl-cyclohexyl.

The term "aryl" shall mean carbocyclic and heterocyclic aromatic groups including, but not limited to, phenyl, 1-naphthyl, 2-naphthyl, fluorenyl, (1,2)-dihydronaphthyl, indenyl, indanyl, thienyl, benzothienyl and thienopyridyl.

The term "heteroaryl" shall mean heterocyclic aromatic groups including, but not limited to thienyl, furyl, benzothienyl and pyridyl.

The term "aralkyl" (also called arylalkyl) shall mean an aryl group appended to an alkyl group including, but not limited to, benzyl, 1-naphthylmethyl, 2-naphthylmethyl, fluorobenzyl, chlorobenzyl, bromobenzyl, iodobenzyl, alkoxybenzyl (wherein "alkoxy" means methoxy, ethoxy, isopropoxy, n-butoxy, sec-butoxy, tert-butoxy an the like), hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl.

The term "acyl" shall mean —(CHO) or —(C=O)-alkyl or —(C=O)-aryl or —(C=O)-aralkyl or —(C=O)-heteroalkyl including, but not limited to, formyl, acetyl, n-propionyl, isopropionyl, n-butyryl, isobutyryl, pivaloyl and benzoyl. Often, acyl denotes an acetyl group.

The term "heteroalkyl" in the context of the present invention denotes (linear, cyclical or branched) alkyl chains where the alkyl chains contain or are substituted with at any position one or more heteroatoms, selected independently from O, S, N, P, Si, Cl, F, Br, I, etc. or groups, selected independently from carboxamide, carboxylic ester, phosphonate ester, hydroxyl, phosphate ester, double or triple bonds, carbamate, urea, thiourea, thiocarbamate, oxime, cyano, carboxyl or carbonyl.

Typical examples are for heteroalkyl groups are:
—S—(CH2)-(CH2)-CO—NH—(CH2)-(CH2)-(CH2)-(CH2)-
—S—(CH2)-(CH2)-CO—NH—(CH2)-(CH2)-(CH2)-
—S—(CH2)-(CH2)-CO—NH—(CH2)-(CH2)-
—S—(CH2)-(CH2)-NH—CO—(CH2)-O—(CH2)-
—S—(CH2)-(CH2)-O—(CH2)-(CH2)-O—(CH2)-(CH2)-S)—(CH2)-(CH2)-
—S—(CH2)-(CH2)-(CH2)-S—(CH2)-(CH2)-(CH2)-

Pol is a polymer. Non-limiting examples for suitable polymers are polyalkyloxy-based polymers like poly(propylene glycol) or poly(ethylene glycol), dextran, chitosan, hyaluronic acid and derivatives, alginate, xylan, mannan, carrageenan, agarose, cellulose, starch, hydroxyethyl starch (HES) and other carbohydrate-based polymers, poly(vinyl alcohols), poly(oxazolines), poly(anhydrides), poly(ortho esters), poly(carbonates), poly(urethanes), poly(acrylic acids), poly(acrylamides) such as poly(hydroxypropyl-methacrylamide) (HMPA), poly(acrylates), poly(methacrylates) like poly(hydroxyethyl-methacrylate), poly(organophosphazenes), poly(siloxanes), poly(vinylpyrrolidone), poly(cyanoacrylates), poly(esters) such as poly(lactic acid) or poly(glycolic acids), poly(iminocarbonates), poly(amino acids) such as poly(glutamic acid), collagen, gelatin, copolymers, grafted copolymers, cross-linked polymers, hydrogels, and block copolymers from the above listed polymers.

The invention also relates to a polymeric compound wherein Pol is selected from poly(propylene glycol), poly(ethylene glycol), starch, hydroxyethyl starch (HES) poly(vinyl alcohols), poly(oxazoline, spoly(acrylic acids), poly(acrylamides), poly(acrylates), poly(methacrylates), poly(organophosphazenes), poly(siloxanes), poly(vinylpyrrolidone), poly(cyanoacrylates), poly(esters), poly(glutamic acid), collagen, or gelatin. Pol is often selected from poly(propylene glycol) and poly(ethylene glycol).

The invention also relates to a polymeric compound wherein Pol is a hydrogel. The invention also relates to a polymeric compound wherein Pol is a branched or hyperbranched polymer. The invention also relates to a polymeric compound wherein Pol is a biopolymer. The invention also relates to a polymeric compound wherein Pol is a protein, preferably an albumin.

The invention also relates to a polymeric compound wherein Pol is a linear or branched poly(ethylene glycol) with a molecular weight between 2,000 Da and 150,000 Dalton. Pol is preferably a linear or branched poly(ethylene glycol) with a molecular weight between 20,000 Da and 80,000 Da.

The invention also relates to a polymeric compound according, wherein E is an exendin, an exendin agonist, an exendin analogue, an exendin derivative, an truncated exendin, a truncated exendin agonist, a truncated exendin derivative, a truncated exendin analogue, GLP-1, a GLP-1 analogue, or a GLP-1 derivative. Preferably E is exendin or an exendin agonist of sequence ID 1 to ID 20, and more preferred E is exendin-3 having sequence ID 2 or exendin-4 having sequence ID 1.

A further aspect of the invention is the use of a polymeric compound as described for the preparation of a medicament, particularly for the treatment of diabetes mellitus or for the prevention of hyperglycemia. Also a medicament for the treatment of obesity or eating disorders can be provided. The invention also relates to the use of a polymeric compound for the preparation of a medicament for the treatment of central nervous system disorders, in particular for the treatment of Alzheimer's disease.

The invention also relates to a pharmaceutical composition comprising at least one polymeric compound as described together with a pharmaceutically acceptable carrier which is useful in a medicine. These compositions are prepared by mixing the polymeric compound with the pharmaceutically acceptable carrier.

The invention also covers a method for the preparation of a polymeric compound of the general formula Pol-L-E, by first attaching the linker L to the exendin or exendin agonist E and then coupling of the polymer Pol to the conjugate L-E. An alternative method for the preparation of a polymeric compound of the general formula Pol-L-E consists of attaching a conjugate Pol-L of the polymer and the linker to the exendin or exendin agonist E.

Hydrogels according to this invention may be defined as three-dimensional, hydrophilic or amphiphilic polymeric networks imbibing large quantities of water. The networks are composed of homopolymers or copolymers, are insoluble due to the presence of covalent chemical or physical (ionic, hydrophobic interactions, entanglements) crosslinks. The crosslinks provide the network structure and physical integrity.

Hydrogels exhibit a thermodynamic compatibility with water which allows them to swell in aqueous media (see. N.

A. Peppas, P. Bures, W. Leobandung, H. Ichikawa, Hydrogels in pharmaceutical formulations, Eur. J. Pharm. Biopharm. 2000, 50, 27-46, WO 2006/003014). The chains of the network are connected in such a fashion that pores exist and that a substantial fraction of these pores are of dimensions of between 1 and 1000 nm. By selecting certain polymerization conditions, the hydrogel may be obtained in the form of an amorphous gel or as beaded resin. Such soft beads may have a diameter of between 1 and 1000 micrometer.

Hydrogels may be synthesized from the polymers and copolymers listed above and physically cross-linked or chemically cross-linked by radical, anionic or cationic polymerization, by chemical reactions like condensation or addition reactions as described in Hennink W. E. and van Nostrum C. F. (2002), Adv. Drug Del. Rev., 54, 13-36.

Further examples include branched and hyperbranched polymers. Examples for such polymers include dendrimers and other dense star polymers. (WO 2005/034909, Esfand R., Tomalia D. A. (2001), Drug Discov Today, 6(8), 427-436; Heegaard P. M., Boas U. (2004), Chem. Soc. Rev. (33(1), 43-63; Grayson S. M., Frechet J. M. (2001), Chem. Rev., 101 (12), 3819-3868).

Pol can also be a biopolymer like a protein. Non-limiting examples of such polymers include albumin, antibodies, fibrin, casein, transferrin and other plasma proteins.

Each Pol polymer can carry one or more biologically active substances linked to the polymer by conjugation with a second prodrug linker as described herein or any other linker known to the person skilled in the art. The polymers may have further substituents and may be functionalized for attachment to the spacer moiety X. Non-limiting examples of such functional groups comprise carboxylic acid and activated derivatives, amino, maleimide, thiol, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl, arylating agents like aryl fluorides, hydroxylamine, disulfides like pyridyl disulfide, vinyl sulfone, vinyl ketone, diazoalkanes, diazoacetyl compounds, epoxide, oxirane, and aziridine.

Preferred functional groups for the Pol polymer include but are not limited to thiol, maleimide, amino, carboxylic acid and derivatives, carbonate and derivatives, carbamate and derivatives, aldehyde, and haloacetyl. Especially preferred functional groups include thiol, maleimide, amino, carboxylic acid and derivatives, carbamate and derivatives, and carbonate and derivatives thereof.

Non-limiting examples for suitable bonds or groups formed between X and Pol include disulfide, S-succinimido, amide, amino, carboxylic ester, sulfonamide, carbamate, carbonate, ether, oxime, hydrazone, urea, thiourea, phosphate, phosphonate, etc.

Preferred bonds or groups formed between X and Pol comprise S-succinimido, amide, carbamate, and urea.

Preferably, the Pol polymers are well hydrated, degradable or excretable, nontoxic and non-immunogenic in mammals. Preferred Pol polymers include polyalkoxy-based polymers like poly(ethylene glycol) and poly(ethylene glycol) reagents as those described in Nektar Inc. 2003 catalog "Nektar Molecule Engineering—Polyethylene Glycol and Derivatives for Advanced PEGylation" and branched, hyperbranched, cross-linked polymers and hydrogels, and proteins like albumin.

Preferred substituents of the compounds according to the invention are:

R2 and R3 are preferably hydrogen or acetyl.

R4 to R12 are preferably selected independently from hydrogen, substituted or non-substituted linear, branched or cyclical $C_1$ to $C_8$ alkyl or heteroalkyl;

R4 to R12 are most preferably hydrogen.

R15 and R16 are selected independently from hydrogen, substituted or non-substituted linear, branched or cyclical alkyl or heteroalkyl, aryls, substituted aryls, substituted or non-substituted heteroaryls, cyano, nitro, halogen, carboxy, carboxyalkyl, alkylcarbonyl, carboxamidoalkyl, etc.

R15 and R16 are most preferably hydrogen.

Each R1 substitution on Ar may be the same or different and is selected independently from hydrogen, substituted or non-substituted linear, branched or cyclical alkyl or heteroalkyl, aryl, substituted aryl, substituted or non-substituted heteroaryl, substituted or non-substituted linear, branched, or cyclical alkoxy, substituted or non-substituted linear, branched, or cyclical heteroalkyloxy, aryloxy, heteroaryloxy, cyano, halogen.

R1 is selected preferably from small substituents such as hydrogen, methyl, ethyl, ethoxy, methoxy, and other C1 to C6 linear, cyclical or branched alkyls and heteroalkyls.

R1 is selected most preferably from methyl, ethyl, propyl, isopropyl, methoxy, ethoxy and hydrogen.

n is zero or a positive integer.

n is preferably zero, one or two.

R13 is e.g. selected from substituted or non-substituted linear, branched or cyclical alkyl or heteroalkyl, aryls, substituted aryls, substituted or non-substituted heteroaryls, R 13 is preferably selected from linear or branched alkyl or heteroalkyl.

R14 is selected from hydrogen, substituted or non-substituted linear, branched or cyclical alkyl or heteroalkyl, aryls, substituted aryls, substituted or non-substituted heteroaryls, Nu-W.

R14 is selected preferably from hydrogen, methyl, ethyl or Nu-W.

W is selected from substituted or non-substituted linear, branched or cyclical alkyl, aryls, substituted aryls, substituted or non-substituted linear, branched or cyclical heteroalkyl, substituted or nonsubstituted heteroaryls.

W is selected preferably from linear or branched alkyls or heteroalkyls.

At least one Nu is present in Nu-W.

Nu is a nucleophile that can perform a nucleophilic attack at the carbonyl carbon of

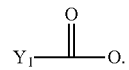

Preferred nucleophiles include primary, secondary and tertiary amino groups, thiol, carboxylic acid, hydroxylamine, hydrazine, and nitrogen containing heteroaryl. Especially preferred nucleophiles include primary, secondary and tertiary amino groups. In order to effectively catalyse the cleavage of the masking group, the spacing between the nucleophile Nu and $Y_1$ is preferably between one and thirteen atoms.

More preferably, the spacing between Nu and $Y_1$ is between two and eight atoms. The at least one nucleophile Nu may be attached anywhere to W (e.g. at the terminus or in the middle of W) or may be part of W.

Preferred variations for Nu-W-Y$_1$ are selected from

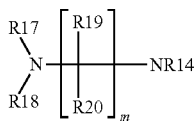

Preferably, R17 to R20 are selected independently from hydrogen, non-substituted alkyl and R17 and/or R18 are not hydrogen.

Most preferably, R19 and R20 are hydrogen.
Most preferably, R17 and R18 are methyl or ethyl.
R14 may also be

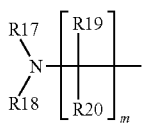

and is preferably not hydrogen.
m is a positive integer.
m is preferably 2 or 3 or 4

Ar of formula Id or Ie is a multi-substituted aromatic hydrocarbon or a multi-substituted aromatic heterocycle. To be aromatic, the number of pi electrons must satisfy the Hückel rule (4n+2) and the cycle has to be planar. A variety of compounds satisfy these criteria and thus are suitable as Ar in formula Id or Ie. The aromatic moieties include:

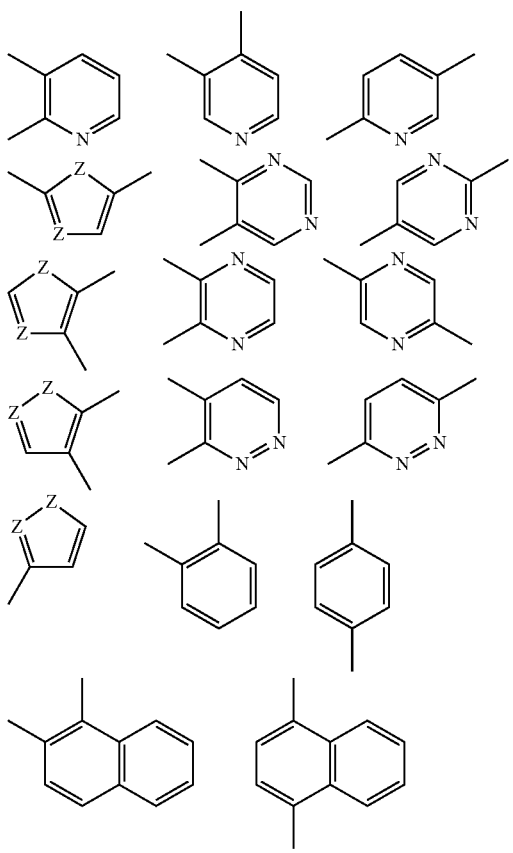

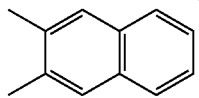

wherein Z in the structures of Ar is O, N, or S, independent from each other.

Preferred moieties for Ar are mono- and dicyclic aromatic hydrocarbons or aromatic heterocycles. Especially preferred moieties are monocyclic five- or six-membered aromatic hydrocarbons or aromatic heterocycles.

Most preferably Ar is a phenyl group.

E is an exendin or exendin agonist. Examples of exendin agonists as used herein are exendin-3 or exendin-4 agonists including but not limited to:
(i) exendin-4 analogues and amidated exendin-4 analogues, in which sequences one or more amino acid residues have been replaced by different amino acid residues including N-terminal modifications,
(ii) truncated exendin-4 and truncated forms that are amidated,
(iii) truncated exendin-4 and truncated forms that are amidated, in which sequences one or more amino acid residues have been replaced by different amino acid residues,
(iv) GLP-1 and amidated GLP-1,
(v) GLP-1-analogues and amidated GlP-1 analogues, in which sequences one or more amino acid residues have been replaced by different amino acid residues including N-terminal modifications,
(vi) truncated GLP-1 and truncated forms that are amidated,
(vii) truncated GLP-1 and truncated forms that are amidated, in which sequences one or more amino acid residues have been replaced by different amino acid residues,
(viii) the already known substances AVE-0010(ZP-10) (Sanofi-Aventis Zealand Pharma), BAY-73-7977 (Bayer), TH-0318, BIM-51077 (Ipsen, Tejin, Roche), N,N-2211 (Novo Nordisk), LY315902.

Structure imide—A suitable example of imide linker is:
A prodrug or a pharmaceutically acceptable salt thereof comprising a drug linker conjugate D-L, wherein
D is a nitrogen containing biologically active moiety; and
L is a non-biologically active linker moiety -L$^1$ represented by formula (I),

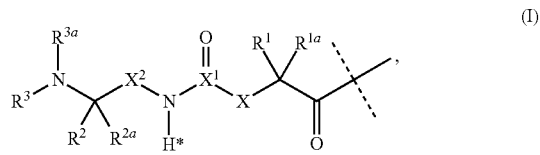

wherein the dashed line indicates the attachment to the nitrogen of the biologically active moiety by forming an amide bond;

X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;

$X^1$ is C; or S(O);

$X^2$ is $C(R^7, R^{7a})$; or $C(R^7, R^{7a})$—$C(R^8, R^{8a})$;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl; or Optionally, one or more of the pairs $R^{1a}/R^{4a}$, $R^{1a}/R^{5a}$, $R^{4a}/R^{5a}$, $R^{4a}/R^{5a}$, $R^{7a}/R^{8a}$ form a chemical bond;

Optionally, one or more of the pairs $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl; or 4 to 7 membered heterocyclyl;

Optionally, one or more of the pairs $R^1/R^4$, $R^1/R^5$, $R^1/R^6$, $R^4/R^5$, $R^7/R^8$, $R^2/R^3$ are joined together with the atoms to which they are attached to form a ring A;

Optionally, $R^3/R^{3a}$ are joined together with the nitrogen atom to which they are attached to form a 4 to 7 membered heterocycle;

A is selected from the group consisting of phenyl; naphthyl; indenyl; indanyl; tetralinyl; $C_{3-10}$ cycloalkyl; 4 to 7 membered heterocyclyl; and 9 to 11 membered heterobicyclyl; and wherein $L^1$ is substituted with one to four groups $L^2$-Z and optionally further substituted, provided that the hydrogen marked with the asterisk in formula (I) is not replaced by a substituent; wherein $L^2$ is a single chemical bond or a spacer; and Z is a carrier group.

Hydrogel—A suitable example of hydrogel linker is:

A polymeric prodrug comprising a hydrogel, a biologically active moiety and a reversible prodrug linker, wherein the prodrug linker covalently links the hydrogel and the biologically active moiety at a position; and the hydrogel has a plurality of pores with openings on the surface of the hydrogel, wherein the diameter of the pores is larger than the biologically active moiety at least at all points of the pore between at least one of the openings and the position of the biologically active moiety.

Exendin agonists mimics the activities of exendin-3 or exendin-4 by binding the receptor(s) at which exendin-3 or exendin-4 exerts its actions which are beneficial as insulinotropic and in the treatment of diabetes mellitus or by mimicking the effects of exendin on urine flow, slowing gastric emptying, inducing satiety, increasing urinary sodium excetion and/or decreasing urinary potassium concentration, by binding to the receptor(s) where exendin cause these effects.

In one embodiment, the exendin or exendin agonists with the Sequence ID NOs: 1-20 can be used to prepare the long acting polymeric conjugates of the invention:

```
Exendin-4
                                          [Seq ID No: 1]
HGEGTFTSDL SKQMEEEAVR LFIEWLKNGG PSSGAPPPS-NH2

Exendin-3
                                          [Seq ID No: 2]
HSDGTFTSDL SKQMEEEAVR LFIEWLKNGG PSSGAPPPS-NH2

[Seq ID No: 3]
HGEGTFTSDL SKQMEEEAVR LFIEWLKNGG P

[Seq ID No: 4]
HGEGTFTSDL SKQMEEEAVR LFIEWLKNGG Y

[Seq ID No: 5]
HGEGTFTSDL SKQMEEEAVR LFIEWLKNGG

[Seq ID No: 6]
HGEGTFTSDL SKQMEEEAVR LFIEWLKNGG-NH2

[Seq ID No: 7]
HGEGTFTSDL SKQMEEEAVR LFIEWLKN-NH2

[Seq ID No: 8]
HGEGTFTSDL SKQLEEEAVR LFIEFLKNGG PSSGAPPPS-NH2

[Seq ID No: 9]
HGEGTFTSDL SKQLEEEAVR LFIEFLKN-NH2

[Seq ID No: 10]
HGEGTFTSDL SKQLEEEAVR LAIEFLKN-NH2

[Seq ID No: 11]
HGEGTFTSDL SKQLEEEAVR LFIEWLKNGG PSSGAPPPS-NH2

[Seq ID No: 12]
HGDGTFTSDL SKQMEEEAVR LFIEWLKNGG PSSGAPPPS-NH2

GLP-1 (7-36) amide
                                          [Seq ID No 13]
HAEGTFTSDV SSYLEGQAAK EFIAWLVKGR-NH2

[Seq ID No 14]
HSEGTFTSDV SSYLEGQAAK EFIAWLVKGR-NH2

GLP-1 (7-37)
                                          [Seq ID No 15]
HAEGTFTSDV SSYLEGQAAK EFIAWLVKGRG

[Seq ID No 16]
HAXaaGTFTSDV SSYLEGQAAK EFIAWLVKGR-NH2
Xaa = P, F, Y

[Seq ID No 17]
HXaaEGTFTSDV SSYLEGQAAK EFIAWLVKGR-NH2
Xaa = T, α-aminobutyric acid, D-Ala, V, Gly

[Seq ID No 18]
HaEGTFTSDV SSYLEGQAAK EFIAWLVKGG

[Seq ID No 19]
R-HAEGTFTSDV SSYLEGQAAK EFIAWLVKGR-NH2
R = acetyl, pyroglutamyl, N-2-hydroxybenzoyl,
N-trans-3-hexenoyl

[Seq ID No 20]
HXaaAEGTFTSDV SSYLEGQAAK EFIAWLVKGR-NH2
Xaa = 6-amino-hexanoyl.
```

Most preferably the exendin is exendin-4 having sequence ID 1.

The exendin and exendin agonists derivatives of the invention will exert any and all activities exhibited by the parent non-modified molecule, but with a prolonged action.

The derivative is administered as a prodrug being essentially non-active biologically but being capable of spontaneous and slow conversion to the original active drug molecule in its bioactive form under physiological conditions in the body, following administration.

Thus, in another aspect, the present invention relates to a pharmaceutical composition comprising an exendin or exendin agonist conjugate of the invention, and a pharmaceutically acceptable carrier. These compositions are in use for any of the uses known for exendin and exendin agonists, for example, for prevention of hyperglycemia and for treatment of diabetes mellitus of any type, e.g. insulin-dependent diabetes mellitus, non insulin dependent diabetes mellitus or gestational diabetes mellitus, for prevention of metabolic syndrome and/or obesity and/or eating disorders, insulin resistance syndrome, lowering plasma lipid level, reducing the cardiac risk, reducing the appetite, reducing the body weight, etc.

The compositions useful in the invention may be presented in any suitable route of administration to humans such as formulations for parenteral, including intravenous, intramuscular and subcutaneous, or for intranasal or oral administration. Suitable pharmaceutically acceptable carriers and excipients can be added by conventional methods known to those skilled in the art, for example as described in Remington: The Science and Practice of Pharmacy, A. R. Gennaro, ed., 20th edition, 2000.

In another aspect, the present invention relates to a method for prevention or treatment of a condition, disease or disorder that can be prevented or treated with an exendin or exendin agonist, which comprises administering to an individual in need an effective amount of an exendin or exendin agonist derivative of the invention.

In one embodiment, the present invention relates to a method for prevention of hyperglycemia which comprises administering to an individual in need an effective insulinotropic amount of exendin or exendin agonist derivative of the invention.

In another embodiment, the present invention provides a method for treatment of diabetes mellitus which comprises administering to an individual in need an effective amount of an exendin or exendin agonist derivative of the invention. The diabetes mellitus may be non-insulin dependent diabetes mellitus, insulin dependent diabetes mellitus, or gestational diabetes mellitus.

In another embodiment, the present invention provides a method for treatment or prevention of metabolic syndrome and/or obesity and/or eating disorders, insulin resistance syndrome, lowering plasma lipid level, reducing the cardiac risk, reducing the appetite, reducing the weight which comprises administering to an individual in need an effective amount of an exendin or exendin agonist conjugate of the invention.

The exendin and exendin conjugates may be obtained as described for GLP-1 conjugates in WO 2006/136586 and WO 2005/099768. In a preferred embodiment the Pol-L-E (preferably wherein the Pol is PEG) has an exendin activity which is less than 5% of the native exendin (E) without the Pol, more preferably less than 3%, even more preferably less than 1% and most preferably virtually inactive.

The activity of the transiently conjugated exendin compounds can be expressed by measuring the glucose lowering effect in db/db mice of their permanently conjugated compound and comparing the permanently conjugated compound's activity to that of native exendin measured as the glucose lowering effect in db/db mice as described in example 17, 18 and 19.

The invention is further illustrated by the following examples and the following figures:

BRIEF DESCRIPTIONS OF THE FIGURES

EXAMPLES

Abbreviations

Figure 1:
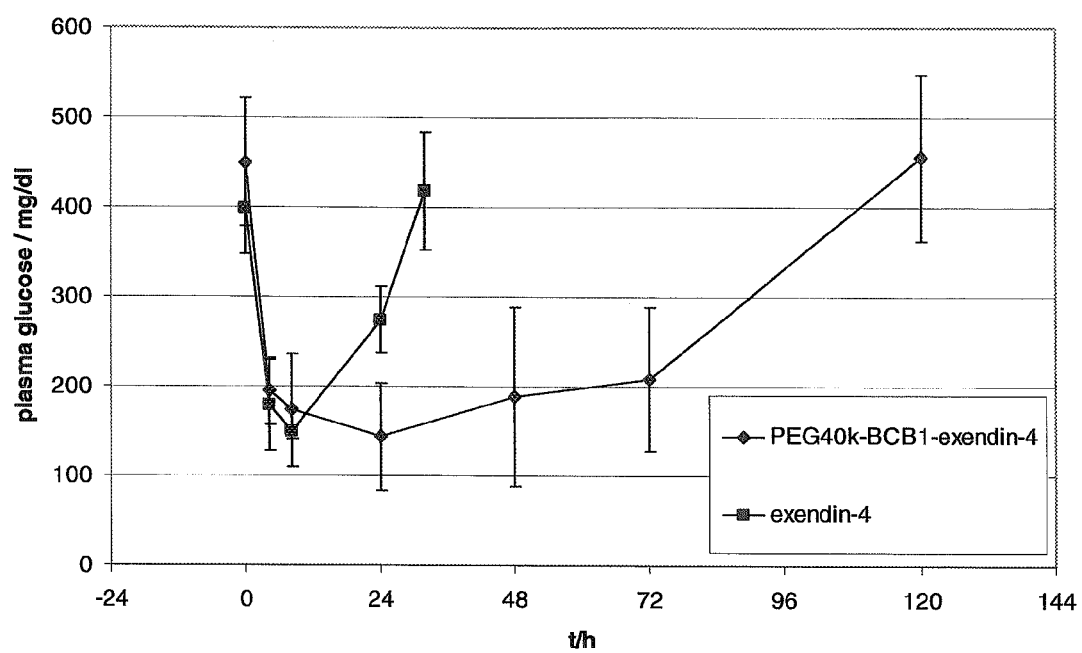
FIG. 1 shows the glucose lowering effect of exendin-4 and PEG40k-BCB1-exendin-4 in db/db mice. The plasma glucose level (mg/dl) is shown as a function of time (hours).

Boc t-butyloxycarbonyl
Bodipy BODIPY® TR-X
Dab 2,4-diaminobutyric acid
DBU 1,3-diazabicyclo[5.4.0]undecene
DCM dichloromethane
(iv) Dde 1-(4,4-dimethyl-2,6-dioxo-cyclohexyliden)-3-methyl-butyl
DIC diisopropylcarbodiimide
DIEA diisopropylethylamine
DMAP dimethylamino-pyridine
DMF N,N-dimethylformamide
DMSO dimethylsulfoxide
Dpr 2,3-diaminopropionic acid
DSC disuccinidylcarbonate
EDTA ethylenediaminetetraacetic acid
eq stoichiometric equivalent
fmoc 9-fluorenylmethoxycarbonyl
HFIP hexafluoroisopropanol
HEPES N-(2-hydroxyethyl)piperazine-N'-(2-ethane-sulfonic acid)
HOBt N-hydroxybenzotriazole
LCMS mass spectrometry-coupled liquid chromatography
LevOH Laevulinic acid
Mal maleimidopropionyl
MS mass spectrum
MW molecular mass
PfpOH pentafluorphenol
PyBOP benzotriazole-1-yl-oxy-tris-pyrrolidino-phosphonium hexafluorophosphate
RP-HPLC reversed-phase high performance liquid chromatography
RT room temperature
SEC size exclusion chromatography
Suc succinimidopropionyl
TES triethylsilane
TFA trifluoroacetic acid.

Materials and Methods

Side chain protected Exendin-4 on Rink amide resin (synthesized by Fmoc-strategy) was obtained from Peptide Specialty Laboratories GmbH, Heidelberg, Germany. Prior to use N-terminal Fmoc protecting group was removed by treating resin 2×10 min with piperidine/DMF 1/4 (v/v).

40 kDa methoxy poly(ethylene glycol) maleimido-propionamide (PEG40K-maleimide) was obtained from Chirotech Technology Ltd, Cambridge, UK.

2-Chlorotrityl chloride resin and amino acids were from Merck Biosciences GmbH, Schwalbach/Ts, Germany, if not stated otherwise. Fmoc-D-homocysteine(Trt)-OH and S-Trityl-3-mercaptopropionic acid (Trt-MPA) were obtained from Bachem AG, Bubendorf, Switzerland. Bodipy-TR-X SE was purchased from Invitrogen GmbH, Karlsruhe, Germany. All other chemicals were from Sigma-ALDRICH Chemie GmbH, Taufkirchen, Germany.

Electrospray ionization mass spectrometry (ESI-MS) was performed on a Waters ZQ 4000 ESI instrument and spectra were, if necessary, interpreted by Waters software MaxEnt.

NMR spectra were recorded on a Bruker AC300.

RP-HPLC was done on 100×20 or 100×40 C18 ReproSil-Pur 3000DS-3 5µ column (Dr. Maisch, Ammerbuch, Germany) connected to a Waters 600 HPLC System and Water2487 Absorbance detector. Linear gradients were used between solution A (0.1% TFA in $H_2O$) and solution B (0.1% TFA in acetonitrile)

Size exclusion chromatography (SEC) was performed using an Amersham Bioscience AEKTAbasic system equipped with a Superdex200 10/300 column (Amersham Bioscience/GE Healthcare), if not stated otherwise.

For Cation Exchange Chromatography, an Amersham Bioscience AEKTAbasic system was equipped with an Source 15S filled HR16/10 column (Amersham Bioscience/GE Healthcare)

Animals. Genetically diabetic mice (db/db mice, strain B6.Cg-m+/+Lepr$^{db}$/J, weight 37-42 g) were obtained from Jackson Laboratories (Bar Harbour, Me., USA). Mice were kept 3 weeks to habituate to vivarium conditions (21-23° C., 45-55% relative humidity, 12:12 hours light:dark cycle with lights on at 7:00 a.m.). Plasma glucose levels were measured using a OneTouch Ultra glucometer (LifeScan Inc., Miliptas Calif., USA).

Example 1

Synthesis of Linker Building Blocks for Those Linkers Undergoing Slow Autohydrolysis

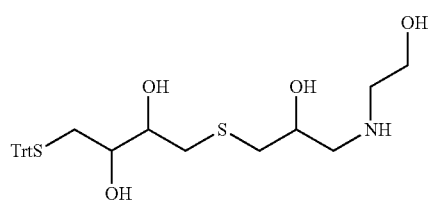

Example 1a

Linker building block 1 was synthesized as described in WO 2006/136586.

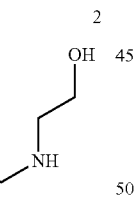

Example 1b

Linker building block 2 was synthesized as described in WO 2006/136586.

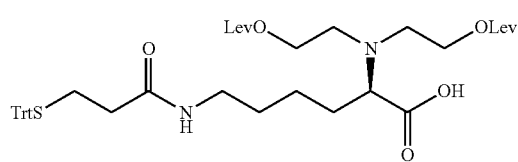

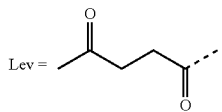

Example 1c

Synthesis of linker building block 3

Trt-MPA (698 mg, 2.0 mmol) was dissolved in 5 ml DCM and mixed with N-hydroxysuccinimide (276 mg, 2.4 mmol), collidine (1.3 ml, 10.0 mmol) and DCC (495 mg, 2.4 mmol). Mixture was stirred for 2 h at RT and a solution of Fmoc-D-Lys-OH.TFA (482 mg, 1.0 mmol), DMAP (41 mg, 0.33 mmol) and DIEA (350 µl, 2.0 mmol) in 1 ml DMF was added and stirred for further 20 min. The mixture was filtered and volatiles were removed in vacuo. Fmoc-D-Lys(Trt-MPA)-OH was purified by RP-HPLC and lyophilized. Yield 368 mg (0.53 mmol). MS: [M+Na]$^+$=468.6 (MW calculated=445.5 g/mol).

Fmoc-D-Lys(Trt-MPA)-OH (368 mg, 0.53 mmol) was immobilized on 2-Chlorotrityl chloride resin (loading 1.1 mmol/g, 479 mg, 0.53 mmol) according to manufacturers instructions and Fmoc protecting group was removed. Bis-hydroxyethylation of free amine was achieved by treating resin 2×2 h with a solution of glycole aldehyde dimer (600 mg, 5.00 mmol), NaCNBH$_3$ (620 mg 10.00 mmol), and 40 µl acetic acid in 4 ml DMF. Resin was washed 5× with DMF.

Resin (0.53 mmol) was incubated 90 min with a mixture of 1.4 g laevulinic acid anhydride and 200 mg DMAP in 4 ml DMF. Resin was washed 5× with DCM and product was cleaved from resin with DCM/HFIP 1/1 (v/v) 3×20 min. Volatiles were removed in vacuo. Linker building block 3 was purified by RP-HPLC and lyophilized. Yield 194 mg (0.25 mmol). MS: [M+Na]$^+$=783.6 (MW calculated=761.0 g/mol).

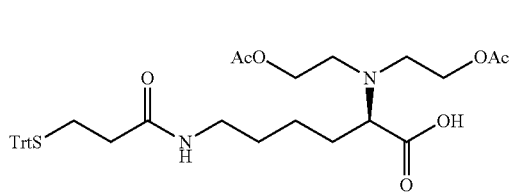

Example 1d

Linker building block 4 was synthesized as described for 3 except for protecting hydroxyl groups as acetate.

For acetylation, resin with hydroxyethyl compound was incubated overnight with a mixture of acetic acid (3 ml), pyridine (3 ml) and DMF (6 ml).

Resin was washed 5× with DMF and 5× with DCM and product was cleaved from resin with DCM/HFIP 1/1 (v/v) 3×20 min. Volatiles were removed in vacuo. Linker building block 4 was purified by RP-HPLC and lyophilized. Yield 76 mg (0.12 mmol). MS: [M+Na]$^+$=671.9 (MW calculated=648.8 g/mol).

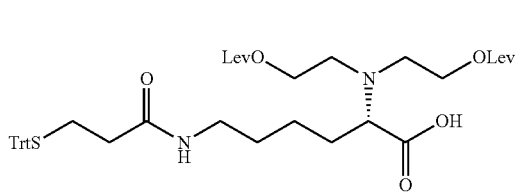

Example 1e

Linker building block 5 was synthesized as described for 3, starting from Fmoc-L-Lys-OH.
Yield 52 mg (0.07 mmol). MS: [M+Na]$^+$=783.7 (MW calculated=761.0 g/mol).

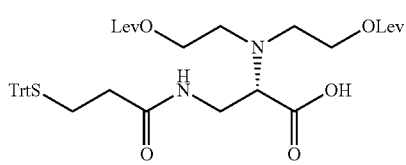

Example 1f

Linker building block 6 was synthesized as described for 3, starting from Fmoc-L-Dpr-OH.
Yield 89 mg (0.12 mmol). MS: [M+Na]$^+$=741.7 (MW calculated=718.9 g/mol).

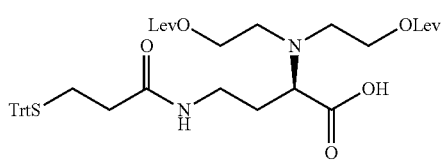

Example 1g

Linker building block 7 was synthesized as described for 3, starting from Fmoc-D-Dab-OH.
Yield 76 mg (0.10 mmol). MS: [M+Na]$^+$=755.9 (MW calculated=732.9 g/mol).

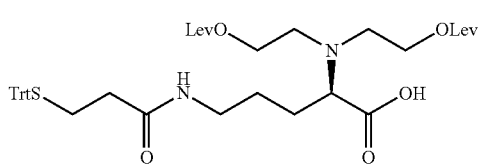

Example 1h

Linker building block 8 was synthesized as described for 3, starting from Fmoc-D-Orn-OH.
Yield 159 mg (0.21 mmol). MS: [M+Na]$^+$=769.6 (MW calculated=746.9 g/mol).

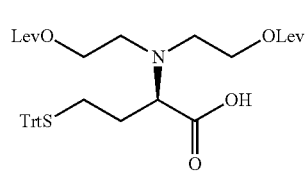

Example 1i

Linker building block 9 was synthesized according to the synthesis of 3. Fmoc-D-Hcy(Trt)-OH was used instead of Fmoc-D-Lys(Trt-MPA)-OH.
Yield 84 mg (0.13 mmol). MS: [M+Na]$^+$=684.6 (MW calculated=661.8 g/mol).

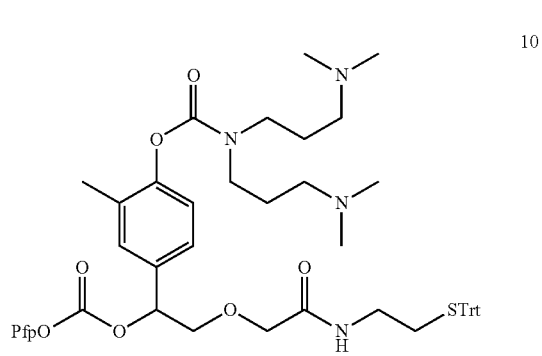

Example 1j

Linker building block 10f was synthesized similar to WO 2005/099768.

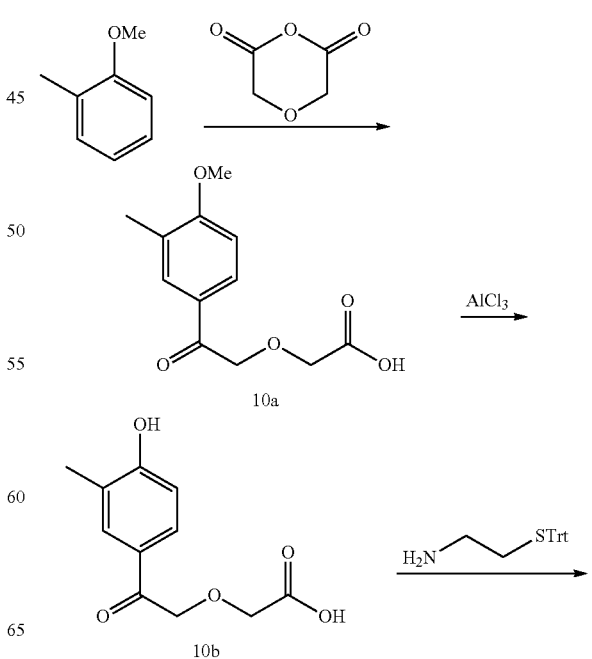

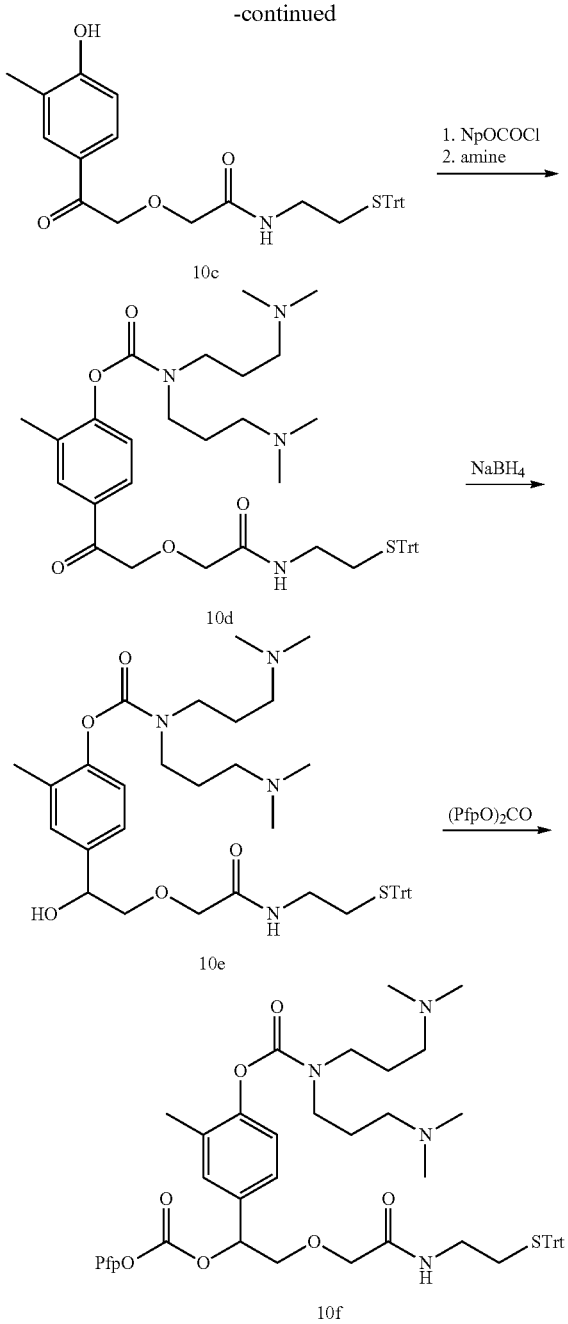

vacuo. Residue was hydrolyzed with 5 M HCl and phenol was extracted twice with ethyl acetate. Organic phase was dried (Na$_2$SO$_4$) and evaporated.

Yield 298 mg, 1.329 mmol). MS: [M+Na]$^+$=247.2 (MW calculated=224.2 g/mol). NMR: (300 MHz, DMSO-d$_6$): δ=12.59 (bs, 1H), 12.25 (s 1H), 7.70 (m, 1H), 7.66-7.63 (m, 1H), 6.85 (d, 1H, J=6.3 Hz), 4.81 (s, 2H), 4.13 (s, 2H), 2.16 (s, 3H).

10b (216 mg, 0.963 mmol), EDC.HCl (203 mg, 1.059 mmol), S-Trityl-cysteamine.HCl (376 mg, 1.059) and collidine (376 µl, 2.889 mmol) were dissolved in 6 ml DCM and stirred at RT for 2 h. 30 ml DCM were added and organic phase was washed twice with 50 ml 1N H$_2$SO$_4$. Organic phase was dried (Na$_2$SO$_4$), evaporated, and amide was purified by silica gel flash chromatography using 5% MeOH and 0.1% AcOH in DCM as eluent.

Yield 221 mg, (0.421 mmol). MS: [M+Na]$^+$=548.5 (MW calculated=525.7 g/mol).

10c (145 mg, 0.277 mmol) was dissolved in 1.5 ml of dry THF. p-Nitrophenyl chloroformate (61 mg, 0.305 mmol) and DIEA (94 µl, 0.554 mmol) were added and the mixture was stirred for 30 min at RT. Bis[3-(dimethylamino)-propyl]-amine (123 µl, 0.554 mmol) was added and stirring was continued for 30 min. Solvent was removed in vacuo, 100 µl of AcOH, 0.5 ml H$_2$O, and 0.5 ml acetonitrile were added and carbamate was purified by RP-HPLC.

Yield 150 mg (0.155 mmol, double TFA salt). MS: [M+Na]$^+$=761.3 (MW calculated=739.0 g/mol).

10d (150 mg, 0.155 mmol, double TFA salt) was dissolved in 3 ml methanol, NaBH$_4$ (29 mg, 0.775 mmol) was added and the mixture was stirred for 10 min at RT. 0.15 ml of acetic acid were added and benzyl alcohol was purified by RP-HPLC.

Yield 131 mg (0.135 mmol). MS: [M+Na]$^+$=763.5 (MW calculated=741.0 g/mol).

10e (118 mg, 0.122 mmol, double TFA salt), (PfpO)$_2$CO (121 mg, 0.307 mmol), DMAP (4 mg, 0.031 mmol) and DIEA (107 µl, 0.614 mmol) were stirred in dry acetonitrile for 10 min at room temperature. After addition of acetic acid (0.5 ml) and water (1 ml) carbonate 10f was purified by RP-HPLC.

Yield 61 mg (0.052 mmol, double TFA salt). MS: [M+Na]$^+$= 974.1 (MW calculated=951.1 g/mol).

Example 2

Synthesis of PEG40k-BCB1-Exendin

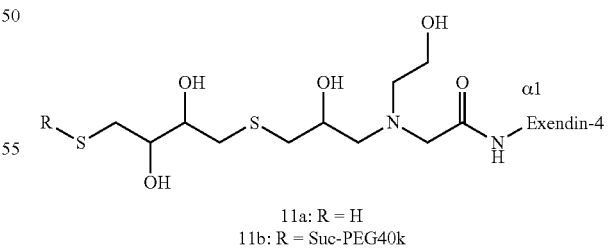

11a: R = H
11b: R = Suc-PEG40k 150 mg side-chain protected Exendin-4 resin (0.11 mmol/g, 16.5 µmol) was suspended in a solution of 84 mg bromoacetic acid (600 µmol) and 94 µl (600 µmol) DIC in 1 ml DMF. The mixture was shaken for 30 min at room temperature. After washing the resin six times with DMF the resin was incubated for 2 h in a solution of 60 mg 1 and 30 µl DIEA in 400 µl DMF. Resin was washed six times each with DMF and In brief, diglycolic anhydride (1.0 g, 8.62 mmol) and AlCl$_3$ (2.3 g, 17.24 mmol) in 10 ml o-methyl anisole were heated to 110° C. for 2 h. Excess o-methyl anisole was removed in vacuo, residue was hydrolized with HCl/ice and mixture was extracted 4 times with ethyl acetate. Organic layers were combined, dried and evaporated. Residue was recrystallized twice from toluene and pure acid was obtained.

Yield 1.47 g, 6.18 mmol). MS: [M+Na]$^+$=261.2 (MW calculated=238.2 g/mol). $^1$H NMR (300 MHz, DMSO-d$_6$): δ=12.56 (bs, 1H), 7.84-7.82 (m, 1H), 7.75 (m, 1H), 7.05 (d, 1H, J=6.6 Hz), 4.85 (s, 2H), 4.14 (s, 2H), 3.88 (s, 3H), 2.19 (s, 3H).

10a (840 mg, 4.72 mmol) was dissolved in 15 ml DCM and AlCl$_3$ (1.41 g, 14.16 mmol) was added. Mixture was stirred for 3 h at 50° C. in a pressure tube. Solvent was removed in DCM. Cleavage of the peptide from resin and removal of protecting groups was achieved with 96/2/2 (v/v/v) TFA/triethylsilane/water for 90 min. Volatiles were removed under nitrogen flow. 11a was purified by RP-HPLC and lyophilized. Yield: 10 mg. MS: $[M+3H]^{3+}=1500.2$, $[M+2H]^{2+}=2250.4$ (MW calculated=4498.0 g/mol)

For PEG conjugation a solution of 11a (1 μmol in 1/1 (v/v) acetonitrile/water (500 μl) was mixed with maleimide-PEG40k (1.7 μmol in 1/1 (v/v) acetonitrile/water (500 μl) and 150 μl of 0.5 M phosphate buffer (pH 7). The mixture was incubated at RT for 10 min. Conjugate 11b was purified by cation exchange chromatography and analyzed by SEC (column: Superdex 200, flow rate, 0.75 ml/min) using 10 mM phosphate buffer (pH 7.4), 150 mM NaCl, and 0.005 Tween 20 as mobile phase.

11b: SEC retention time: 14 min

Example 3

Synthesis of PEG40k-BCB2-Exendin

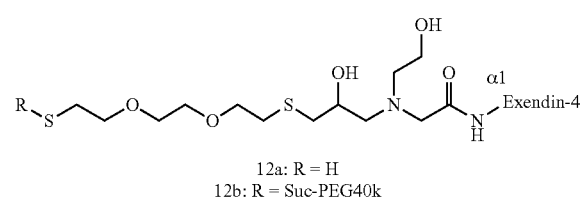

12a: R = H
12b: R = Suc-PEG40k

Compounds 12a and 12b were synthesized according to Example 2 using building block 2.

Example 4

Synthesis of PEG40k-BCB3-Exendin

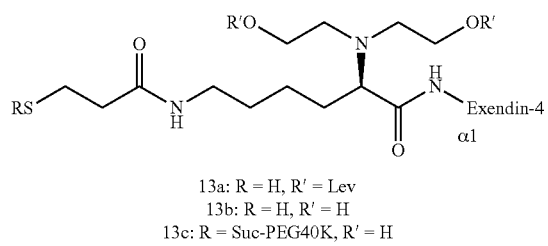

13a: R = H, R' = Lev
13b: R = H, R' = H
13c: R = Suc-PEG40K, R' = H 100 mg side-chain protected Exendin-4 resin (0.11 mmol/g, 11.0 μmol) was added to a solution of 23 mg (30 μmol) 3, 15.6 mg (30 μmol) PyBOP, 4.6 mg (30 μmol) HOBT, and 13 μl (75 μmol) DIEA in 1 ml DMF. The mixture was shaken for 30 min at room temperature. Resin was washed six times each with DMF and DCM. Cleavage of the peptide from resin and removal of protecting groups was achieved with 96/2/2 (v/v/v) TFA/triethylsilane/water for 90 min. Volatiles were removed under nitrogen flow. Crude 13a was precipitated in ice-cooled ether and incubated for 20 min in a solution of 33/33/32/2 (v/v/v/v) acetonitrile/water/0.5 M PO$_4$ pH 6.5/N$_2$H$_4$ hydrate adjusted with HCl to pH 7.0. 13b was purified by RP-HPLC and lyophilized. Yield: 9.5 mg 13b. MS: $[M+3H]^{3+}=1497.8$, $[M+2H]^{2+}=2246.5$ (MW calculated=4491.0 g/mol)

For PEG conjugation a solution of 13b (1 μmol) in 1/1 (v/v) acetonitrile/water (500 μl) was mixed with maleimide-PEG40k (1.7 μmol) in 1/1 (v/v) acetonitrile/water (500 μl) and 150 μl of 0.5 M phosphate buffer (pH 7). The mixture was incubated at RT for 10 min. Conjugate 13c was purified by cation exchange chromatography and analyzed by SEC (column: Superdex 200, flow rate, 0.75 ml/min) using 10 mM phosphate buffer (pH 7.4), 150 mM NaCl, and 0.005 Tween 20 as mobile phase.

13c: SEC retention time: 14 min

Example 5

Synthesis of PEG40k-BCB4-Exendin

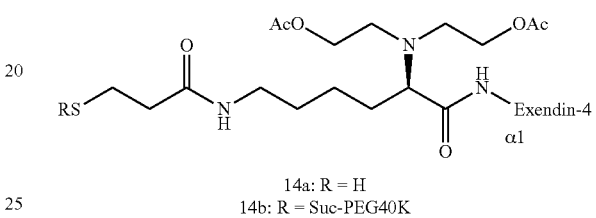

14a: R = H
14b: R = Suc-PEG40K 50 mg side-chain protected Exendin-4 resin (0.11 mmol/g, 5.5 μmol) was suspended in a solution of 13 mg (20 μmol) 4, 7.6 mg (20 μmol) HATU, and 7 μL (40 μmol) DIEA in 1 ml DMF. The mixture was shaken for 30 min at room temperature.

Resin was washed six times each with DMF and DCM. Cleavage of the peptide from resin and removal of protecting groups was achieved with 96/2/2 (v/v/v) TFA/triethylsilane/water for 90 min. Volatiles were removed under nitrogen flow and 14a was purified by RP-HPLC and lyophilized. Yield: 4.0 mg 14a. MS: $[M+3H]^{3+}=1525.0$, $[M+2\mu l]^{2}=2286.8$ (MW calculated=4575.1 g/mol)

For PEG conjugation a solution of 14a (1 μmol) in 1/1 (v/v) acetonitrile/water (500 μl) was mixed with maleimide-PEG40k (1.7 μmol) in 1/1 (v/v) acetonitrile/water (500 μl and 150 μl of 0.5 M phosphate buffer (pH 7). The mixture was incubated at RT for 10 min. Conjugate 14b was purified by cation exchange chromatography and analyzed by SEC (column: Superdex 200, flow rate, 0.75 ml/min) using 10 mM phosphate buffer (pH 7.4), 150 mM NaCl, and 0.005 Tween 20 as mobile phase.

14b: SEC retention time: 14 min

Example 6

Synthesis of PEG40k-BCB5-Exendin

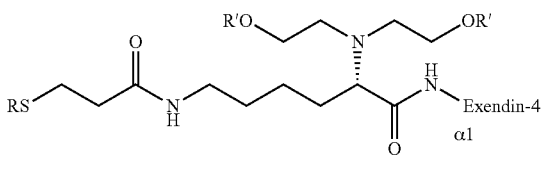

15a: R = H, R' = Lev
15b: R = H, R' = H
15c: R = Suc-PEG40K, R' = H

Compounds 15a, 15, and 15c were synthesized according to Example 4 from 50 mg side-chain protected Exendin-4 resin (0.11 mmol/g, 5.5 µmol) and 5.

Yield: 9.0 mg 15b. MS: $[M+3H]^{3+}=1497.5$, $[M+2H]^{2+}=2245.0$ (MW calculated=4491.0 g/mol)

Example 7

PEG40k-BCB6-Exendin

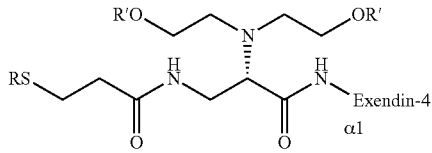

16a: R = H, R' = Lev
16b: R = H, R' = H
16c: R = Suc-PEG40k, R' = H

Compounds 16a, 16b, and 16c were synthesized according to Example 4 from 50 mg side-chain protected Exendin-4 resin (0.11 mmol/g, 5.5 µmol) and 6.

Yield: 8.0 mg 16b. MS: $[M+3H]^{3+}=1483.2$, $[M+2H]^{2+}=2225.8$ (MW calculated=4448.9 g/mol)

Example 8

PEG40k-BCB7-Exendin

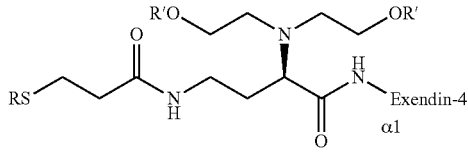

17a: R = H, R' = Lev
17b: R = H, R' = H
17c: R = Suc-PEG40k, R' = H

Compounds 17a, 17b, and 17c were synthesized according to Example 4 from 50 mg side-chain protected Exendin-4 resin (0.11 mmol/g, 5.5 µmol) and 7.

Yield: 8.0 mg 17b. MS: $[M+3H]^{3+}=1488.2$, $[M+2H]^{2+}=2231.8$ (MW calculated=4462.9 g/mol)

Example 9

PEG40k-BCB8-Exendin

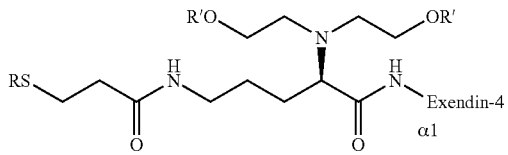

18a: R = H, R' = Lev
18b: R = H, R' = H
18c: R = Suc-PEG40k, R' = H

Compounds 18a, 18b, and 18c were synthesized according to Example 4 from 50 mg side-chain protected Exendin-4 resin (0.11 mmol/g, 5.5 µmol) and 8.

Yield: 6.0 mg 18b. MS: $[M+3H]^{3+}=1492.1$, $[M+2H]^{2+}=2239.2$ (MW calculated=4477.0 g/mol)

Example 10

PEG40k-BCB9-Exendin

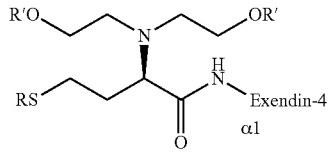

19a: R = H, R' = Lev
19b: R = H, R' = H
19c: R = Suc-PEG40k, R' = H

Compounds 19a, 19b, and 19c were synthesized according to Example 4 from 50 mg side-chain protected Exendin-4 resin (0.11 mmol/g, 5.5 µmol) and 9.

Yield: 7.0 mg 19b. MS: $[M+3H]^{3+}=1465.4$, $[M+2H]^{2+}=2196.8$ (MW calculated=4391.9 g/mol)

Example 11

Synthesis of PEG40k-CB3-Exendin

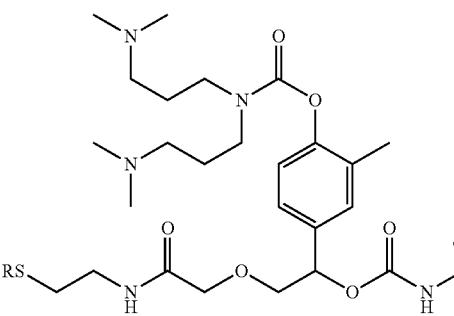

20a: R = H
20b: R = Suc-PEG40k 200 mg side-chain protected Exendin-4 resin (0.11 mmol/g, 22 µmol) were suspended in a solution of 30 mg 10f, 20 µl DIEA and 4 mg DMAP in 1 ml DMF. The mixture was shaken for 2 h at room temperature. Resin was washed six times each with DMF and DCM. Cleavage of the peptide from resin and removal of protecting groups was achieved with 96/2/2 (v/v/v) TFA/triethylsilane/water for 90 min. Volatiles were removed under nitrogen flow. 20a was purified by RP-HPLC and lyophilized. Yield: 25.4 mg. MS: $[M+3H]^{3+}=1571.5$, $[M+4H]^{4+}=1179.0$ (MW calculated=4711.3 g/mol).

For PEG conjugation a solution of 20a (1.4 mol) in 1/1 (v/v) acetonitrile/water (500 µl was mixed with maleimide-PEG40k (2.1 µmol in 1/1 (v/v) acetonitrile/water (500 µl and 150 µl of 0.5 M phosphate buffer (pH 7). The mixture was incubated at RT for 10 min. Conjugate 20b was purified by cation exchange chromatography and analyzed by SEC (column: Superdex 200, flow rate, 0.75 ml/min) using 10 mM phosphate buffer (pH 7.4), 150 mM NaCl, and 0.005% Tween 20 as mobile phase.

20b: SEC retention time: 14 min

Example 12

Synthesis of Permanent PEG40k-Exendin

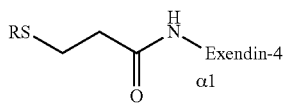

21a: R = H
21b: R = Suc-PEG40k 150 mg side-chain protected Exendin-4 resin (0.11 mmol/g, 16.5 µmol) were suspended in a solution of 30 mg S-Trityl-mercaptopropionic acid, 50 mg PyBOP and 30 µl DIEA in 1 ml DMF. The mixture was shaken for 1 h at room temperature. Resin was washed six times each with DMF and DCM. Cleavage of the peptide from resin and removal of protecting groups was achieved with 96/2/2 (v/v/v) TFA/triethylsilane/water for 90 min. Volatiles were removed under nitrogen flow. 21a was purified by RP-HPLC and lyophilized. Yield: 13.5 mg. MS: $[M+3H]^{3+}$=1425.6, (MW calculated=4274.7 g/mol).

For PEG conjugation a solution of 21a (1.15 µmol) in 1/1 (v/v) acetonitrile/water (500 µl) was mixed with maleimide-PEG40k (1.6 µmol) in 1/1 (v/v) acetonitrile/water (500 µL) and 150 µl of 0.5 M phosphate buffer (pH 7). The mixture was incubated at RT for 10 min. Conjugate 21b was purified by cation exchange chromatography and analyzed by SEC (column: Superdex 200, flow rate, 0.75 ml/min) using 10 mM phosphate buffer (pH 7.4), 150 mM NaCl, and 0.005 Tween 20 as mobile phase.

21b: SEC retention time: 14 min

Example 13

Synthesis of Permanent PEG-exendin-4-$N^{\epsilon 27}$-fluorescein

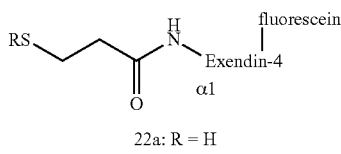

22a: R = H
22b: R = Suc-PEG40k 150 mg side-chain protected exendin-4-$N^{\epsilon 27}$(ivDde) resin (0.10 mmol/g, 15.0 µmol) were suspended in a solution of 30 mg S-Trityl-mercaptopropionic acid, 50 mg PyBOP and 30 µl DIEA in 1 ml DMF. The mixture was shaken for 1 h at room temperature. Resin was washed six times with DMF and incubated three times 10 min with 2% Hydrazine in DMF (v/v) and washed again six times with DMF. Resin was agitated with 3 eq 5(6)-carboxy-fluorescein NHS ester (21.3 mg, 45 µmol) and DIEA (8 µl, 45 µmol) in DMF for 30 min. Resin was washed six times each with DMF and DCM. Cleavage of the peptide from resin and removal of protecting groups was achieved with 96/2/2 (v/v/v) TFA/triethylsilane/water for 90 min. Volatiles were removed under nitrogen flow. 22a was purified by RP-HPLC and lyophilized. Yield: 13.5 mg. MS: $[M+3H]^{3+}$=1545.1, (MW calculated=4633 g/mol).

For PEG conjugation a solution of 22a (1.2 mol) in 1/1 (v/v) acetonitrile/water (500 µl) was mixed with maleimide-PEG40k (1.7 µmol in 1/1 (v/v) acetonitrile/water (500 µl and 150 µl of 0.5 M phosphate buffer (pH 7). The mixture was incubated at RT for 10 min. Conjugate 22b was purified by cation exchange chromatography and analyzed by SEC (column: Superdex 200, flow rate, 0.75 ml/min) using 10 mM phosphate buffer (pH 7.4), 150 mM NaCl, and 0.005 Tween 20 as mobile phase.

22b: SEC retention time: 14 min

Example 14

Synthesis of Permanent PEG40k-Bodipy 23

50 µl 3 mM Bodipy-NHS ester (Molecular Probes) in DMSO were mixed with 10 mg cystamine dihydrochloride in 150 µl DMSO and 10 µl DIEA. The solution was incubated for 30 min and than 30 mg DTT were added. 3 ml 0.5 M sodium phosphate buffer pH 7 were added and the solution was incubated for 10 min. The Bodipy-SH intermediate was purified by RP-HPLC and lyophilized. Yield: 0.54 mg (900 nmol). MS: [M+Na]=619.9, (MW calculated=597.5 g/mol).

The Bodipy-SH intermediate was dissolved in 0.5 ml 1/1 (v/v) water/acetonitrile and 50 mg PEG40-maleimide in 1.5 ml 1/1 (v/v) water/acetonitrile and 0.5 ml sodium phosphate buffer pH 7 were added.

The solution was incubated for 20 min at room temperature and than 2 µl mercaptoethanol were added. The product was purified by SEC. Yield 28 mg (700 nmol).

Example 15

Release of Exendin-4 from Conjugate 11b, 12b, 13c, 15, c16c, 17c, 18c, 19c, and 20b In Vitro Release of Exendin-4 from conjugates 11b, 12b, 13c, 15, c16c, 17c, 18c, 19c, and 20b was effected by hydrolysis in buffer (15 mM HEPES, 150 mM NaCl, 3 mM EDTA, 0.005% Tween 20) at pH 7.4 and 37° C. Samples were taken at time intervals and analyzed by RP-HPLC. Peaks correlating with the retention time of Exendin-4 were integrated and plotted against incubation time, and curve-fitting software was applied to estimate the corresponding half-life of release.

TABLE 1

Table 1: Polymeric prodrug hydrolysis

| Compound | $t_{1/2}$ buffer pH 7.4, 37° C. |
|---|---|
| 11b | 160 h |
| 12b | 240 h |
| 13c | 40 d |
| 15c | 50 d |
| 16c | 25 d |
| 17c | 40 d |
| 18c | 50 d |
| 19c | 30 d |
| 20b | 140 h |

(time of half-life in hours (h) and days (d))

Example 16

In Vitro Stability of 14b 3 mg 14b was dissolved in 6 ml 10 mM acetate buffer, 0.2% phenol at pH 4.0 and 2 ml aliquots were incubated at 4° C., RT, and 40° C., respectively. Samples were taken at time intervals and analyzed by RP-HPLC. After 5 weeks at 40° C. no release of exendin-4 was observed.

Example 17

Glucose Lowering Effect of Native Exendin-4 in Diabetic db/db Mice

Exendin-4 (6.0 nmol/mouse in 160 µl PBS buffer pH 7.2) was administered to db/db mice (n=3) subcutaneously and plasma glucose levels were determined at various time points. Plasma glucose reached within 8 h a minimum of 149±7 mg/dl and returned to initial values after 30 h (FIG. 1).

Example 18

Glucose Lowering Effect of PEG40K-BCB1-Exendin 11b in Diabetic db/db Mice

The glucose lowering effect of exendin-4 releasing PEG40k-BCB1-exendin-4 11b was assessed by subcutaneously administering conjugate (6.0 nmol/mouse in 125 µl PBS buffer pH 7.2) to db/db mice (n=5). In order to ensure comparability, sampling time points were the same as for native exendin-4 and permanent PEGylated PEG40k-exendin-4 (Example 19).

Plasma glucose fell to 173±63 mg/dl after 8 h, rose slight to 209±80 mg/dl at 72 h and returned to initial values at 120 h (FIG. 1).

Example 19

Figure 2:
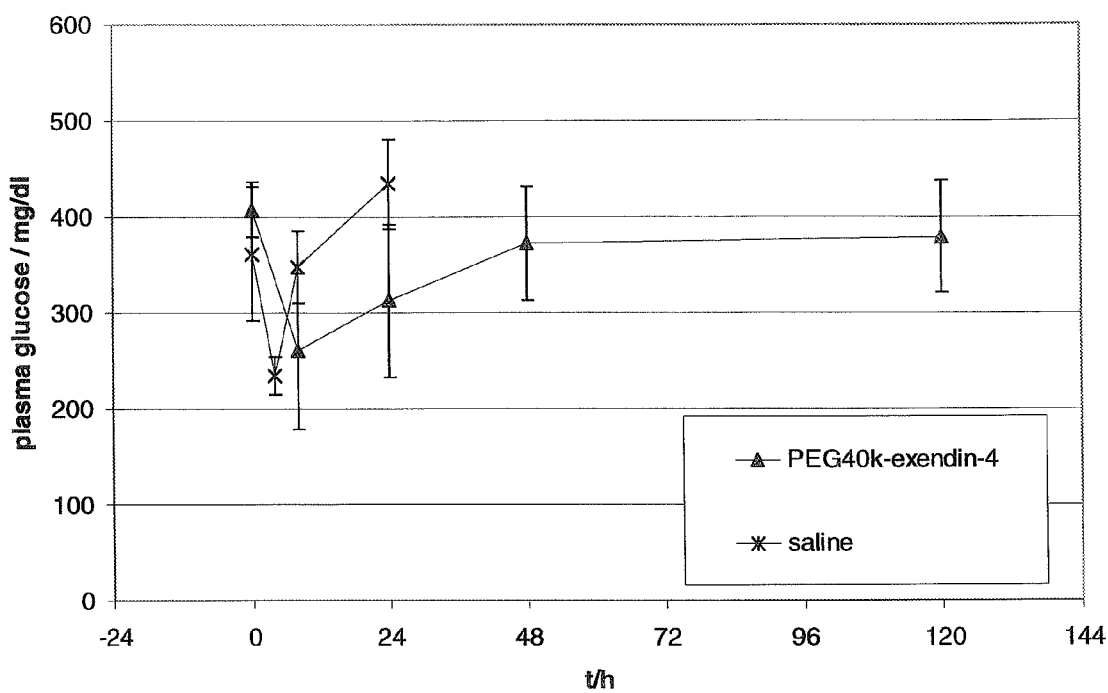
FIG. 2 shows the absence of glucose lowering effects of saline and PEG40k-exendin-4 in db/db mice. The plasma glucose level (mg/dl) is shown as a function of time (hours).

Glucose Lowering Effect of Permanent PEG40k-Exendin-4 in Diabetic db/db Mice and Saline Negative Control Permanent PEGylated PEG40k-exendin-4 21b (6.0 nmol/mouse) was administered to db/db mice (n=5) subcutaneously in 100 µl PBS buffer pH 7.2. A decline in plasma glucose concentration (260±82 mg/dl) was observed after 8 h. This effect is comparable to saline negative control (n=3) and is a consequence of intraday glucose variation due to night/day feeding behavior (FIG. 2).

Example 20

PK Studies of Conjugate 11b, 20b, and 21b in Rat

Figure 3:
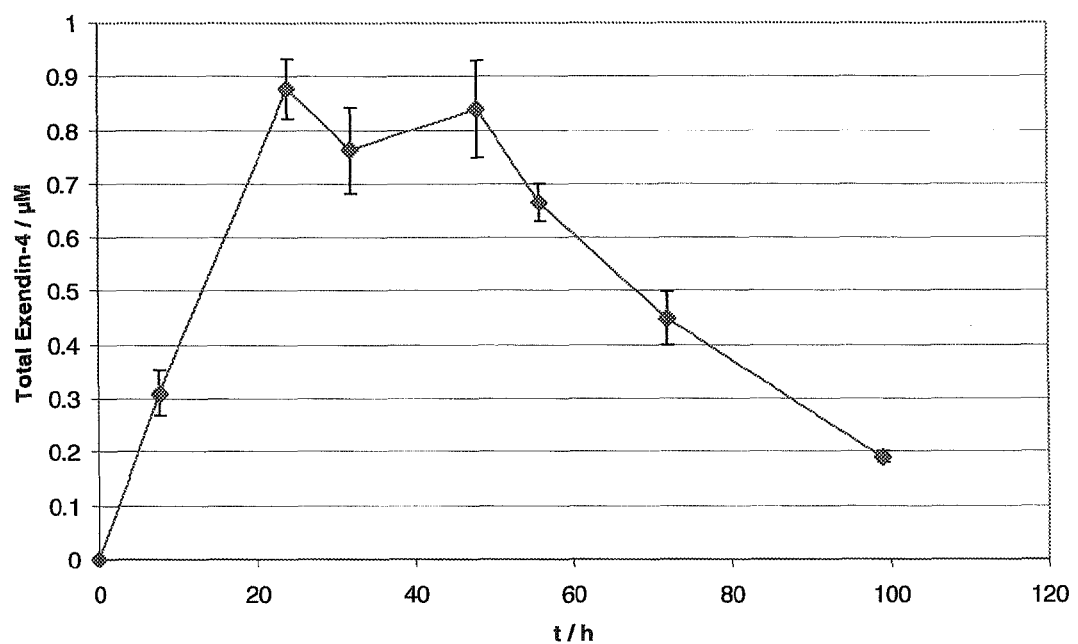
FIG. 3 shows the pharmacokinetics of transient PEG40k-BCB1-exendin-4 in rat. The total exendin-4 concentration (µM) is shown as a function of time (hours).
Figure 4:
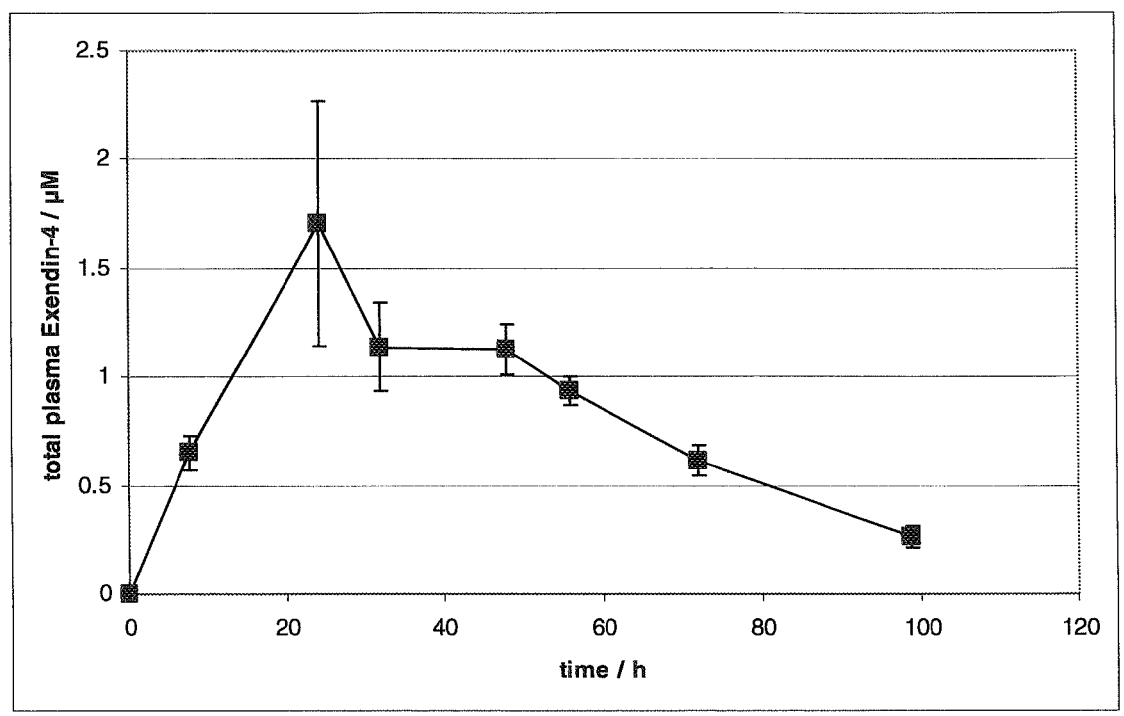
FIG. 4 shows the pharmacokinetics of transient PEG40k-CB3-exendin-4 in rat. The total plasma exendin-4 concentration (µM) is shown as a function of time (hours).
Figure 5:
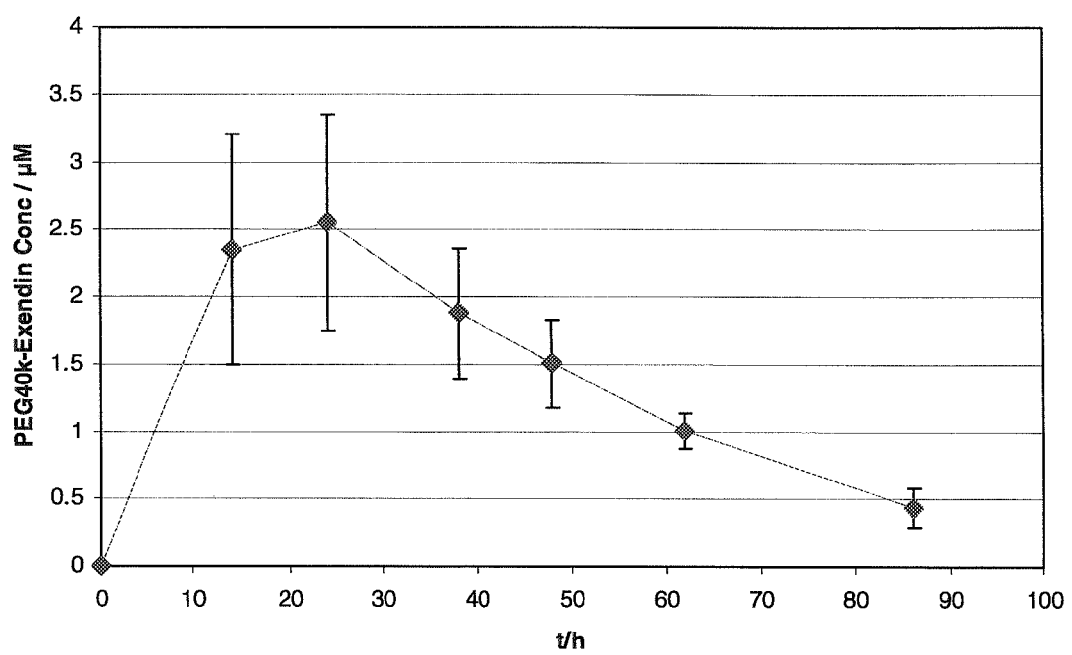
FIG. 5 shows the pharmacokinetics of transient PEG40k-exendin-4 in rat. The PEG40k-exendin-4 concentration (µM) is shown as a function of time (hours).

The pharmacokinetics of transient PEG40K-BCB1-exendin 11 b (FIG. 3), transient PEG40K-CB3-exendin 20b (FIG. 4), and permanent PEG40k-exendin 21b (FIG. 5) were assessed by subcutaneously administering 0.5 µmol/kg conjugate in 850 µl PBS buffer pH 7.2 to SD Rats (330-350 g, male, n=3 each) Plasma samples were analyzed for total exendin-4 using an exendin-4 EIA (Phoenix Pharmaceutical Inc., Burlingame, USA). It was verified that Exendin-4 and PEG40k-Exendin-4 conjugates showed the same response in this assay. Due to the relatively short half-life of exendin-4 of 33 min in rats (Copley 2006), EIA signals reflect mainly PEG40k-linker-exendin-4 conjugate pharmacokinetics.

All conjugates showed Tmax values of about 24 h and terminal half-lives of about 24 h.

Example 21

Stability of PEG40k-exendin-4-$N^{\epsilon 27}$-fluorescein In Vivo

PEG40k-exendin-4-$N^{\epsilon 34}$-fluorescein and PEG40k-bodipy (125 nmol each, in 600 µl PBS buffer pH 7.2) were coinjected subcutaneously into SD rats (260-290 g, n=3)

Figure 6:
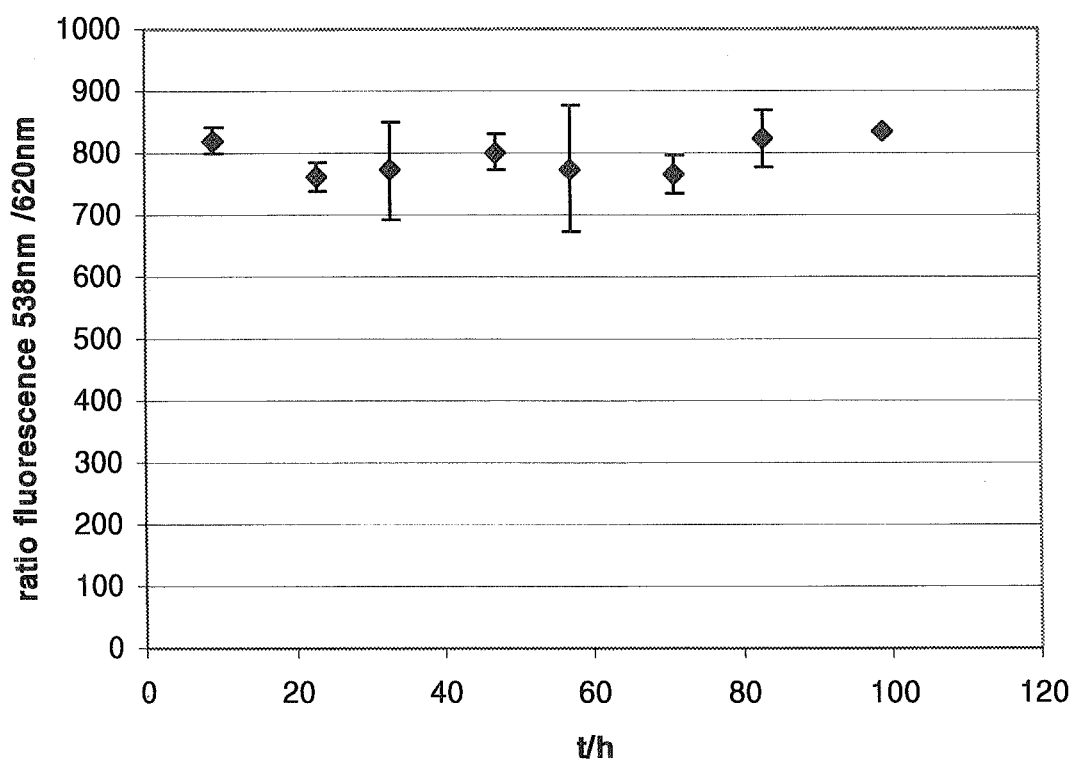
FIG. 6 shows the absence of protease digestion of permanent PEG40k-exendin-4 in rat (ratio fluorescence 538 nm/620 nm as a function of time (hours)).

Plasma samples were analyzed for fluorescence of fluorescein (Ex 485 nm, Em 538 nm) and Bodipy (Ex 584 nm, Em 620 nm). Ratio of Em 538/Em 620 was almost the same at each time point, showing the absence of proteolysis between residues 1-27 in PEG40k-exendin-4-1$N^{\epsilon 27}$-fluorescein (FIG. 6).

---

The invention claimed is:

1. A polymeric compound of the general formula (I)

Pol-L-E    (I)

wherein Pol is a polymer,
wherein L is a releasing linker capable of undergoing autohydrolysis and is a non-biologically active linker moiety -$L^1$ represented by formula (Ia),

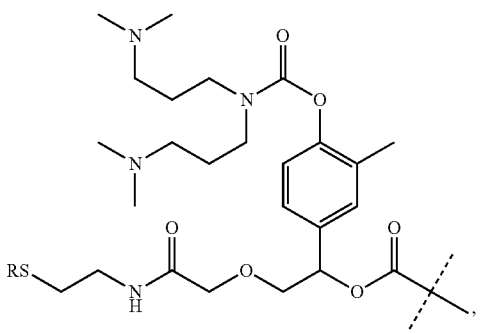

wherein the dashed line indicates attachment to a nitrogen atom of a biologically active moiety by forming an amide bond,
wherein R is substituted with one group $L^2$-Pol,
wherein $L^2$ is a single chemical bond or a spacer,
wherein E is exendin or an exendin agonist,
and wherein the bond between L and E is hydrolysed under in vivo conditions at a pH-value between 7.0 and 7.5 at a temperature of 36° to 38° C. in human plasma with a half-life of 24 hours or more.

2. A polymeric compound according to claim 1, wherein Pol is a polyalkyloxy-based polymers, L is a releasing linker consisting of neighbouring groups catalyzing hydrolysis of a transient linkage and E is exendin or an exendin agonist, wherein the bond between L and E is hydrolysed under in vivo conditions at a pH-value between 7.0 and 7.5 at a temperature of 36° C. to 38° C. in human plasma with a half-life between 24 hours and 100 days.

3. A polymeric compound according to claim 1 wherein Pol is selected from poly(propylene glycol), poly(ethylene glycol), starch, hydroxyethyl starch (HES) poly(vinyl alcohols), poly(oxazoline, poly(acrylic acids), poly(acrylamides), poly(acrylates), poly(methacrylates), poly(organophosphazenes), poly(siloxanes), poly(vinylpyrrolidone), poly(cyanoacrylates), poly(esters), poly(glutamic acid), collagen, and gelatin.

4. A polymeric compound according to claim 1 wherein Pol is a hydrogel.

5. A polymeric compound according to claim wherein Pol is a branched or hyperbranched polymer.

6. A polymeric compound according to claim wherein Pol is a biopolymer.

7. A polymeric compound according to claim wherein Pol is a protein.

8. A polymeric compound according to claim 1 wherein Pol is a linear or branched poly(ethylene glycol) with a molecular weight between 2,000 Da and 150,000 Da.

9. A polymeric compound according to claim 1 wherein Pol is a linear or branched poly(ethylene glycol) with a molecular weight between 20,000 Da and 80,000 Da.

10. A polymeric compound according to claim 1, wherein E is an exendin or exendin agonist selected from the group consisting of
   (i) exendin-4 analogues and amidated exendin-4 analogues, in which sequences one or more amino acid residues have been replaced by different amino acid residues including N-terminal modifications,
   (ii) truncated exendin-4 and truncated forms that are amidated,
   (iii) truncated exendin-4 and truncated forms that are amidated, in which sequences one or more amino acid residues have been replaced by different amino acid residues,
   (iv) GLP-1 and amidated GLP-1,
   (v) GLP-1-analogues and amidated GLP-1 analogues, in which sequences one or more amino acid residues have been replaced by different amino acid residues including N-terminal modifications,
   (vi) truncated GLP-1 and truncated forms that are amidated,
   (vii) truncated GLP-1 and truncated forms that are amidated, in which sequences one or more amino acid residues have been replaced by different amino acid residues; and
   (viii) AVE-0010(ZP-10), BAY-73-7977, TH-0318, BIM-51077, NN-2211 and LY315902.

11. A polymeric compound according to claim 1, wherein E is an exendin or an exendin agonist of SEQ ID No 1 to SEQ ID No 20.

12. A polymeric compound according to claim 1, wherein E is exendin-3 having SEQ ID No 2 or exendin-4 having SEQ ID No 1.

13. A pharmaceutical composition comprising at least one polymeric compound according to claim 1 together with a pharmaceutically acceptable carrier which is useful in a medicine.

* * * * *

SEQUENCE LISTING

```
<160> NUMBER OF SEQ ID NOS: 20

<210> SEQ ID NO 1
<211> LENGTH: 39
<212> TYPE: PRT
<213> ORGANISM: artificial
<220> FEATURE:
<223> OTHER INFORMATION: Heloderma suspectum
<220> FEATURE:
<221> NAME/KEY: MOD_RES
<222> LOCATION: (39)..(39)
<223> OTHER INFORMATION: AMIDATION

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

```
<210> SEQ ID NO 2
<211> LENGTH: 39
<212> TYPE: PRT
<213> ORGANISM: Heloderma HORRIDUM
<220> FEATURE:
<221> NAME/KEY: MOD_RES
<222> LOCATION: (39)..(39)
<223> OTHER INFORMATION: AMIDATION

<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 31
<212> TYPE: PRT
<213> ORGANISM: artificial
<220> FEATURE:
<223> OTHER INFORMATION: Exendin/Exendin agonist

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 4
<211> LENGTH: 31
<212> TYPE: PRT
<213> ORGANISM: artificial
<220> FEATURE:
<223> OTHER INFORMATION: Exendin/Exendin agonist

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Tyr
            20                  25                  30

<210> SEQ ID NO 5
<211> LENGTH: 30
<212> TYPE: PRT
<213> ORGANISM: artificial
<220> FEATURE:
<223> OTHER INFORMATION: Exendin/Exendin agonist

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 6
<211> LENGTH: 30
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (30)..(30)
<223> OTHER INFORMATION: AMIDATION
```

```
<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 7
<211> LENGTH: 28
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (28)..(28)
<223> OTHER INFORMATION: AMIDATION

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 8
<211> LENGTH: 39
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (39)..(39)
<223> OTHER INFORMATION: AMIDATION

<400> SEQUENCE: 8

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 9
<211> LENGTH: 28
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (28)..(28)
<223> OTHER INFORMATION: AMIDATION

<400> SEQUENCE: 9

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 10
<211> LENGTH: 28
<212> TYPE: PRT
<213> ORGANISM: artificial
<220> FEATURE:
<223> OTHER INFORMATION: Exendin/Exendin agonist
```

```
<220> FEATURE:
<221> NAME/KEY: MOD_RES
<222> LOCATION: (28)..(28)
<223> OTHER INFORMATION: AMIDATION

<400> SEQUENCE: 10

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 11
<211> LENGTH: 39
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (39)..(39)
<223> OTHER INFORMATION: AMIDATION

<400> SEQUENCE: 11

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (39)..(39)
<223> OTHER INFORMATION: AMIDATION

<400> SEQUENCE: 12

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 13
<211> LENGTH: 30
<212> TYPE: PRT
<213> ORGANISM: artificial
<220> FEATURE:
<223> OTHER INFORMATION: GLP-1(7-37)
<220> FEATURE:
<221> NAME/KEY: MOD_RES
<222> LOCATION: (30)..(30)
<223> OTHER INFORMATION: AMIDATION

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

```
<210> SEQ ID NO 14
<211> LENGTH: 30
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (30)..(30)
<223> OTHER INFORMATION: AMIDATION

<400> SEQUENCE: 14

His Ser Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 15
<211> LENGTH: 31
<212> TYPE: PRT
<213> ORGANISM: artificial
<220> FEATURE:
<223> OTHER INFORMATION: GLP-1(7-37)

<400> SEQUENCE: 15

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 16
<211> LENGTH: 30
<212> TYPE: PRT
<213> ORGANISM: artificial
<220> FEATURE:
<223> OTHER INFORMATION: Exendin/Exendin agonist
<220> FEATURE:
<221> NAME/KEY: VARIANT
<222> LOCATION: (3)..(3)
<223> OTHER INFORMATION: Pro, Phe or Tyr
<220> FEATURE:
<221> NAME/KEY: MOD_RES
<222> LOCATION: (30)..(30)
<223> OTHER INFORMATION: AMIDATION

<400> SEQUENCE: 16

His Ala Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 17
<211> LENGTH: 30
<212> TYPE: PRT
<213> ORGANISM: artificial
<220> FEATURE:
<223> OTHER INFORMATION: Exendin/Exendin agonist
<220> FEATURE:
<221> NAME/KEY: VARIANT
<222> LOCATION: (2)..(2)
<223> OTHER INFORMATION: Tyr, alpha aminobutyric acid (Abu), Val, D-Ala
     or Gly
<220> FEATURE:
<221> NAME/KEY: MOD_RES
<222> LOCATION: (30)..(30)
<223> OTHER INFORMATION: AMIDATION

<400> SEQUENCE: 17
```

```
His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 18
<211> LENGTH: 30
<212> TYPE: PRT
<213> ORGANISM: artificial
<220> FEATURE:
<223> OTHER INFORMATION: Exendin/Exendin agonist

<400> SEQUENCE: 18

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly
            20                  25                  30
```

<210> SEQ ID NO 19
<211> LENGTH: 30
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (1)..(1)
<223> OTHER INFORMATION: Modification: acetyl, pyroglutamyl,
      N-2-hydroybenzoyl, N-trans-3-hexenoyl
<220> FEATURE:
<221> NAME/KEY: MOD_RES
<222> LOCATION: (30)..(30)
<223> OTHER INFORMATION: AMIDATION

<400> SEQUENCE: 19

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

<210> SEQ ID NO 20
<211> LENGTH: 31
<212> TYPE: PRT
<213> ORGANISM: artificial
<220> FEATURE:
<223> OTHER INFORMATION: Exendin/Exendin agonist
<220> FEATURE:
<221> NAME/KEY: MOD_RES
<222> LOCATION: (2)..(2)
<223> OTHER INFORMATION: Xaa: 6-aminohexanoyl
<220> FEATURE:
<221> NAME/KEY: MOD_RES
<222> LOCATION: (31)..(31)
<223> OTHER INFORMATION: AMIDATION

<400> SEQUENCE: 20

```
His Xaa Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30
```